United States Patent
Yamanaka et al.

(10) Patent No.: US 8,435,449 B2
(45) Date of Patent: May 7, 2013

(54) CHEMICAL SUBSTANCE SENSING ELEMENT, CHEMICAL SUBSTANCE SENSING APPARATUS, AND METHOD OF MANUFACTURING CHEMICAL SUBSTANCE SENSING ELEMENT

(75) Inventors: Mikihiro Yamanaka, Osaka (JP); Katsutoshi Takao, Osaka (JP); Tomohisa Kawata, Osaka (JP); Norie Matsui, Osaka (JP); Shuhji Nishiura, Osaka (JP); Keita Hara, Osaka (JP); Yasuaki Murashi, Osaka (JP); Jun Kudo, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 821 days.

(21) Appl. No.: 12/528,388

(22) PCT Filed: Mar. 4, 2008

(86) PCT No.: PCT/JP2008/053867
§ 371 (c)(1),
(2), (4) Date: Nov. 10, 2009

(87) PCT Pub. No.: WO2008/108371
PCT Pub. Date: Sep. 12, 2008

(65) Prior Publication Data
US 2010/0086439 A1 Apr. 8, 2010

(30) Foreign Application Priority Data
Mar. 5, 2007 (JP) .................................. 2007-054851

(51) Int. Cl.
*G01N 27/04* (2006.01)
(52) U.S. Cl.
USPC .................... 422/98; 422/88; 422/90; 422/91; 977/957
(58) Field of Classification Search .................... 422/88, 422/90, 91, 98; 977/957
See application file for complete search history.

(56) References Cited

U.S. PATENT DOCUMENTS

| 6,346,189 | B1 | 2/2002 | Dai et al. |
| 2005/0176029 | A1 | 8/2005 | Heller et al. |
| 2006/0003437 | A1 | 1/2006 | Fujihara et al. |
| 2008/0283875 | A1 | 11/2008 | Mukasa et al. |

FOREIGN PATENT DOCUMENTS

| JP | 9-243590 | 9/1997 |
| JP | 2003-322653 | 11/2003 |
| JP | 2004-28798 | 1/2004 |
| JP | 2005-238388 | 9/2005 |
| JP | 2008-216083 | 9/2008 |
| WO | WO 01/44796 | 6/2001 |
| WO | WO 2005/040755 | 5/2005 |
| WO | WO 2006/134942 | 12/2006 |

OTHER PUBLICATIONS

J.S. Ye et al., Electrochemical Biosensing Platforms Using Phthalocyanine-Functionalized Carbon Nanotube Electrode, 17 Electroanalysis 89-96 (2005).*
International Search Report for PCT/JP2008/053867 mailed May 27, 2008.
Xing-Jiu Huang et al, "Ferrocene Functionalized Single-Walled Carbon Nanotube Bundles, Hybrid Interdigitated Construction Film for L-Glutamate Detection", J. Phys. Chem., vol. 111, (2007), pp. 1200-1206.
Jian-Shan YE et al., "Electrochemical Biosensing Platforms using Phthalocyanine-Functionalized Carbon Nanotube Electrode", Electroanalysis, vol. 17, No. 1, (Jan. 2005), pp. 89-96.
Jacob . Wohlstadter, Carbon Nanotube-Based Biosensor, Advanced Materials, vol. 15, No. 14, (Aug. 19, 2003), pp. 1184-1187.
Hee Cheul Choi et al., Carbon Nanotube Platform for Fluorescence Based Biosensor Systems, Proceedings of SPIE, Nanosesing: Materials and Devices II, vol. 6008, (2005), pp. 600804.1-600804.7.
Zhenyu Sun et al., Synthesis of Zr-02-Carbon Nanotube Composites and Their Application as chemiluminescent Sensor Material for Ethanol., J. Phys. Chem. B, vol. 110, No. 27, (Jun. 20, 2006), pp. 13410-13414.
Wenqing Cao et al., "Breath Analysis: Potential for Clinical Diagnosis and Exposure Assessment", Clinical Chemistry, vol. 52.5, (2006), pp. 800-811.
Ri'ichiro Saito, Outline and Problems of Carbon Nano Tube, Kinou Zxairyou (Functional Material), vol. 21, No. 5, (May 2001), p. 6-14.

* cited by examiner

*Primary Examiner* — Randy Boyer
(74) *Attorney, Agent, or Firm* — Nixon & Vanderhye, P.C.

(57) ABSTRACT

A chemical substance sensing element 142 for detecting a specific chemical substance included in biological information includes a carbon nanostructure and, because of metal complex or a fluorescent molecule modifying its surface, exhibits substance selectivity and high sensitivity. Of the substances modifying the surface of carbon nanostructures, CoPc reacts with NO and pentane and DAF-2 reacts with NO, as the components contained in the biological information, respectively, and both produce reaction products. The reaction product derived from CoPc changes electric resistance between nodes 154 and 156, and the reaction product derived from DAF-2 generates fluorescence of a specific wavelength when irradiated with excitation light. Therefore, by measuring the change in electric resistance or presence/absence and wavelength of fluorescent of the present element, sensing of NO or pentane is possible.

6 Claims, 11 Drawing Sheets

FIG. 5
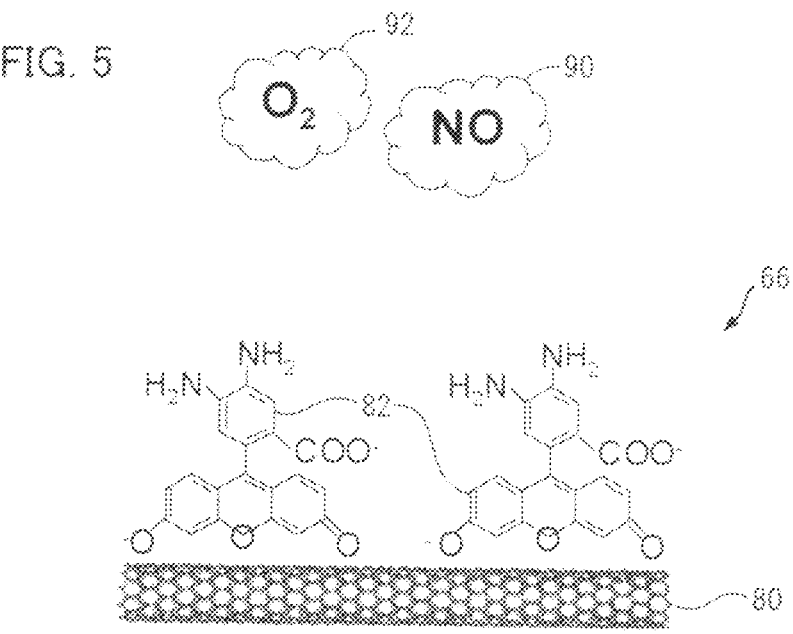
(A)
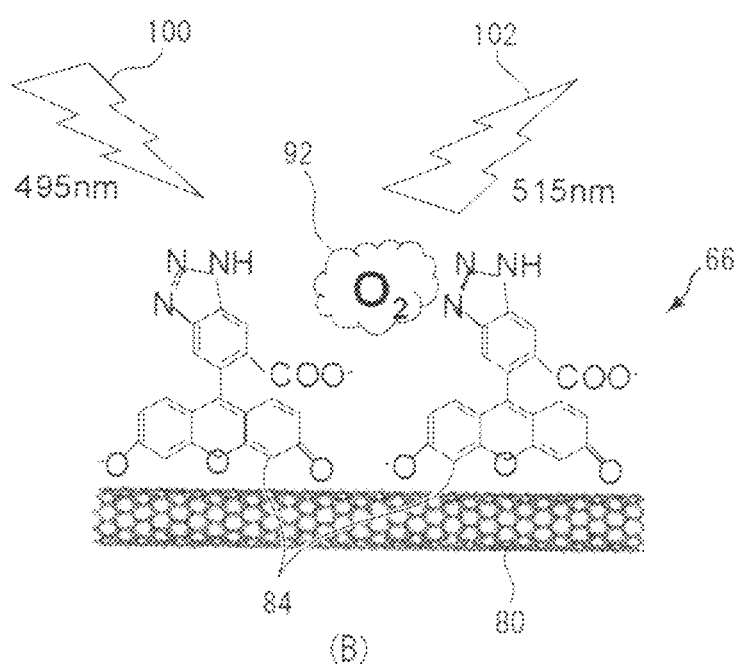
(B)

FIG. 7
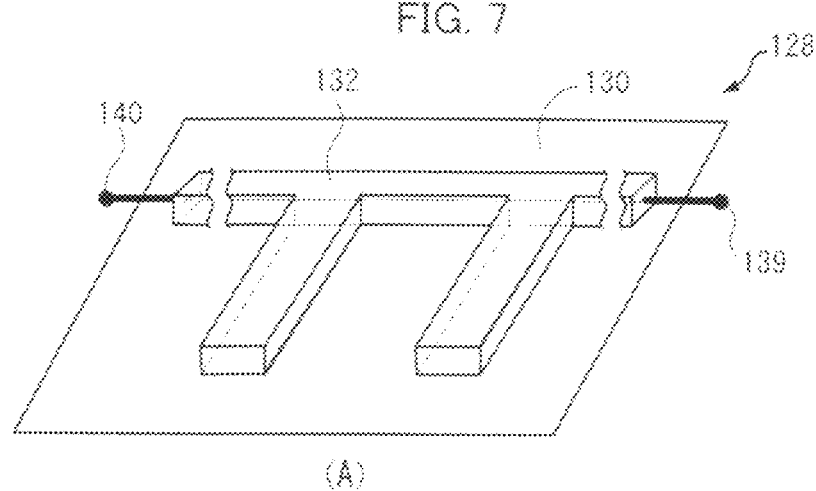
(A)
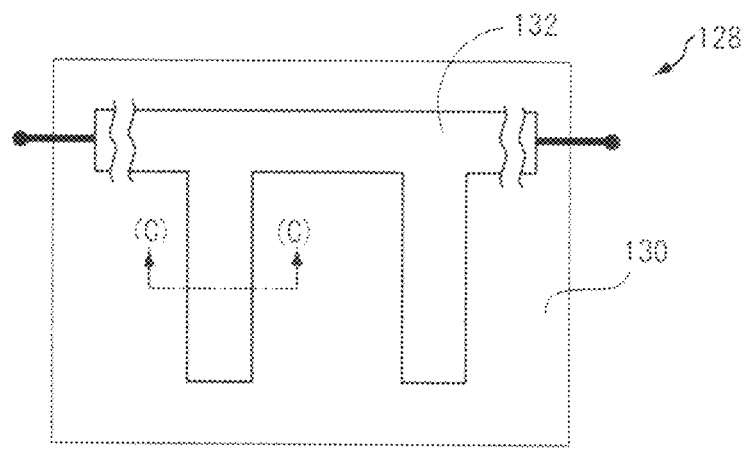
(B)
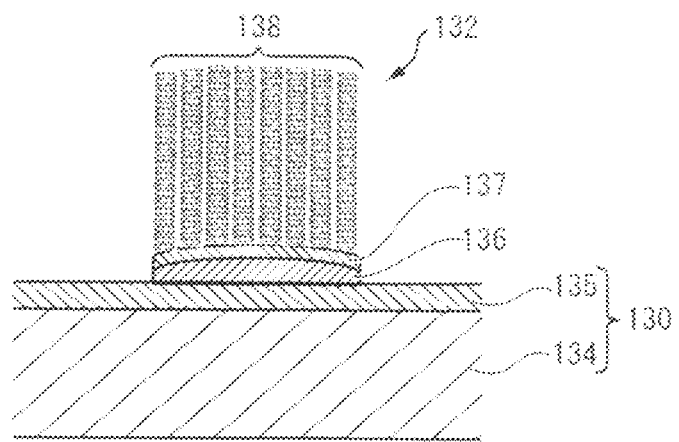
(C)

FIG. 8
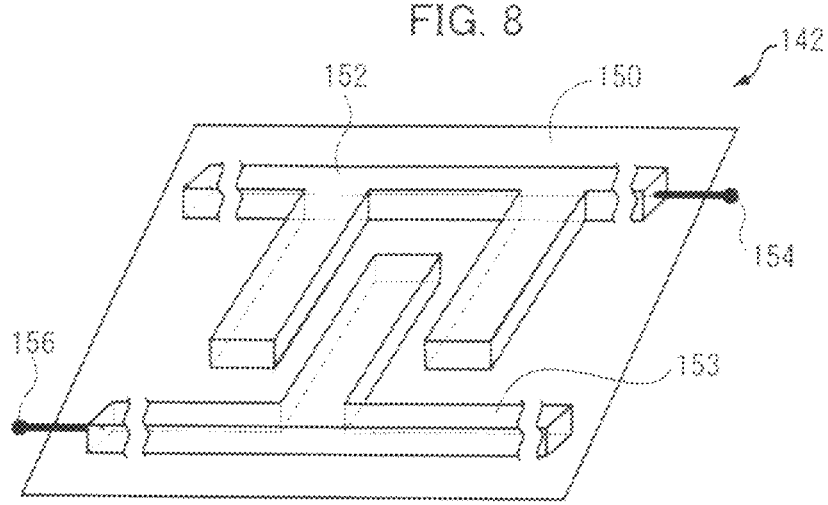
(A)
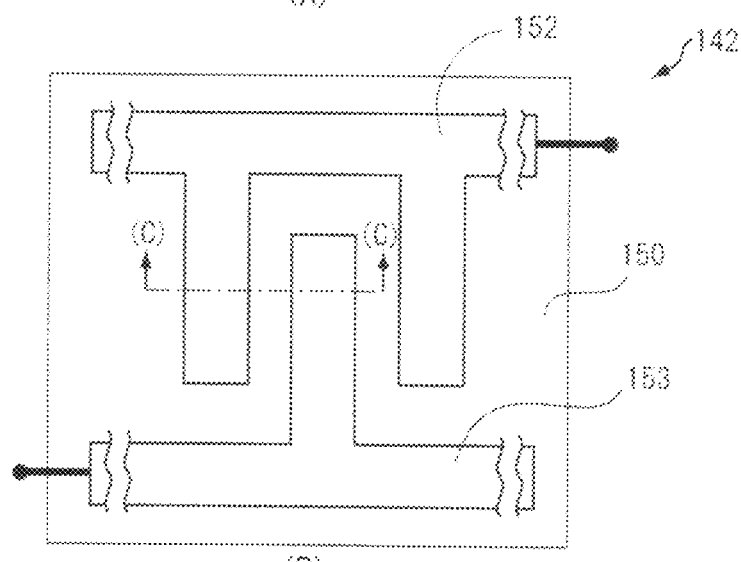
(B)
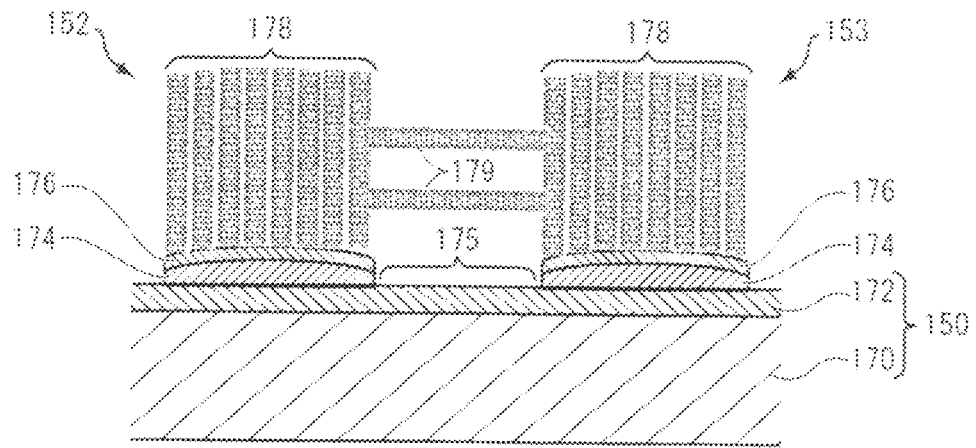
(C)

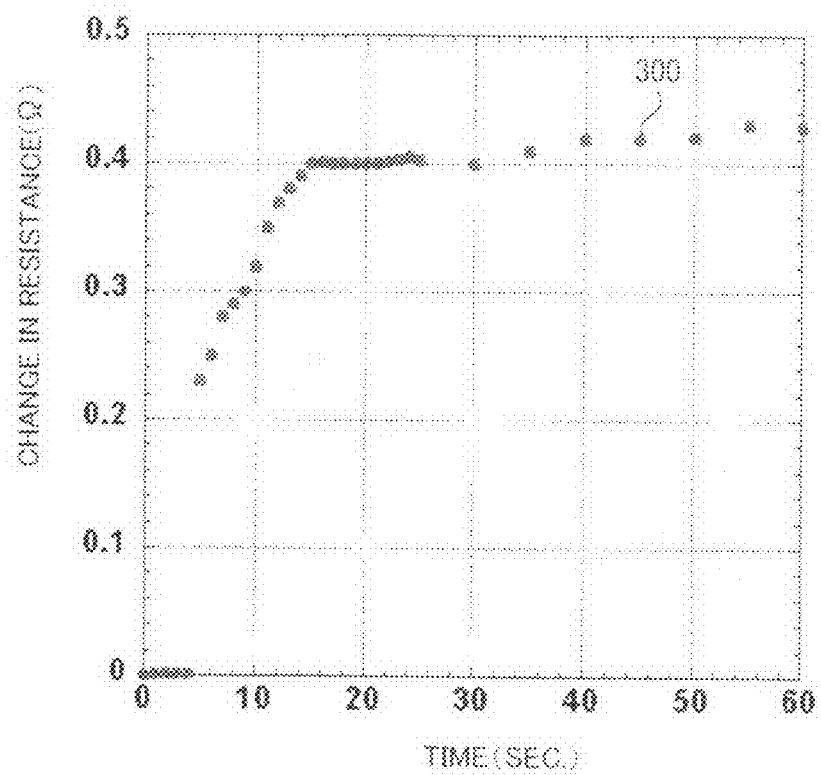

ized structure. The graphite structure continued two-dimensionally is referred to as a
CHEMICAL SUBSTANCE SENSING ELEMENT, CHEMICAL SUBSTANCE SENSING APPARATUS, AND METHOD OF MANUFACTURING CHEMICAL SUBSTANCE SENSING ELEMENT This application is the U.S. national phase of International Application No. PCT/JP2008/053867 filed 4 Mar. 2008, which designated the U.S. and claims priority to Japan Application No. 2007-054851 filed 5 Mar. 2007, the entire contents of each of which are hereby incorporated by reference.

TECHNICAL FIELD

The present invention relates to an element for sensing a chemical substance in gaseous and liquid biological samples to check human health condition and, more specifically, to a technique of improving selectivity and sensitivity to a gas as a sensing object of a sensing element utilizing a carbon isotope having a nanostructure (hereinafter referred to as a "carbon nanostructure") including carbon nano tube and carbon nano fiber.

BACKGROUND ART

Now, Japan faces an aging society, which involves increasing cost of medical care. Accordingly, sound management of medical insurance system becomes increasingly difficult. These and other related problems draw growing interest in health management and disease prevention in the society. What is desired is a society focusing more heavily on preventive care (here, such a society will be referred to as "preventive-care-oriented society") than cures after development of diseases.

To attain such an object, a system that allows handy and speedy checking of one's health condition is necessary. Biological information that can easily be sampled for grasping one's health condition includes blood, urine, sweat, saliva and expired gas. Among various components of these, a certain substance generates or its volume changes as a sign of potential disease or as a result of some disease that one suffers from, and by knowing variation thereof, it is highly possible to grasp one's health condition. Such a substance is called a marker. Marker monitoring helpfully leads to early detection and rapid cure.

Non-Patent Document 1 discusses relations between diseases and markers. Table 1 shows part of the relations.

TABLE 1

| Biological Information | Disease | | |
|---|---|---|---|
| | Large Classification | Small Classification | Marker |
| Expired gas | Oxidant stress | Lipid oxidation, asthma, bronchial infection | Ethane, pentane, H2O2 |
| | Pulmonary disease | Asthma, chronic obstructive pneumonia | NO, CO, H2O2 |
| | Gastrointestinal disease | Indigestion, gastritis, duodenal ulcer | H2, carbon isotope |
| | Metabolic abnormality | Diabetes | Acetone |
| | Kidney disease | | Ammonia |
| | Periodontal disease | | Mercaptan |

TABLE 1-continued

| Biological Information | Disease | | |
|---|---|---|---|
| | Large Classification | Small Classification | Marker |
| Saliva, Urine | Stress | | Globulin A, cortisol, amylase, chromogranin A, immune globulin |
| Sweat | Fatigue | | Ammonia |
| Tear | Fatigue | | ACTH |

Of the biological information, expired gas exists close to the blood in capillary vessel separated only by a thin membrane in the lung and, therefore, it particularly contains many markers. Further, its sampling is easy. Therefore, it is the most useful biological information to be monitored.

As a method of monitoring these markers in the expired gas, a gas sensing element may be available. Conventionally, an oxide semiconductor gas sensor using tin oxide has been known. The lower detection limit of sensor sensitivity is at the level of down to $10^3$ ppm, and for monitoring, it is necessary to heat the sample to about 300° C. As regards the monitoring of expired gas, according to Non-Patent Document 1, high sensitivity with lower detection limit at the level of ppb is necessary. Further, the expired gas is highly prone to change when heated, and non-invasive method is desired. Therefore, for this purpose, an oxide semiconductor gas sensor is inappropriate. To satisfy social demand, higher performance is necessary.

As a solution to such a problem, Non-Patent Document 2, which will be described later, proposes a gas sensor formed of recently discovered carbon nano tube (hereinafter denoted as "CNT").

CNT is a tubular carbon material whose diameter is on the nano order. A crystal structure having a plate-shaped structure of regular hexagons bonded together, each consisting of six carbon atoms, is called a graphite structure. The graphite structure continued two-dimensionally is referred to as a graphane sheet. CNT has a structure formed by rolling the graphane sheet to a cylinder. CNT has a very stable structure and exhibits electric conductivity allowing high-speed electron migration derived from Π electron coupling therein, and it is known to be a conductor superior to metal wires depending on the structure.

According to Non-Patent Document 2, when chemical substance molecules adhere to CNT, electron migration occurs, and electromotive force generates. In other words, between two points on CNT, difference in potentials or change in electric resistance occurs. By detecting the change in electric resistance, the chemical substance can be sensed. Further, since CNT has a miniature structure on the nano order, significant improvement can be expected in responsiveness and detection lower limit. Specifically, the time from when the specific chemical substance adheres to the CNT surface until electric resistance of CNT changes is very short because of the conductivity and nanostructure of CNT, as compared with the conventional sensing element described above. Further, since CNT has large surface area and has such a structure that every atom constitutes the surface, the influence of substance adsorption is reflected on the change in electric resistance with only a little loss resulting from electron scattering and the like. Therefore, CNT is believed to enable adsorption and confirmation of presence of specific chemical substance of a small amount, which have been difficult by a conventional sensing element.

Further, because of the nanostructure of CNT, the chemical substance sensing element using the CNT realizes a very compact, low-power consumption and portable element, which is optimal for a simple means for checking individual health condition.

As a general sensor using CNT, one such as described in Patent Document 1 has been known. This reference, however, does not include any description related to monitoring of markers included in biological information as described above, and details of sensor sensitivity are not described, either.

Non-Patent Document 1: Wenqing Cao et al., "Breath Analysis: Potential for Clinical Diagnosis and Exposure Assessment," Clinical Chemistry, vol. 52. 5, p. 800-811, 2006

Non-Patent Document 2: Ri'ichiro SAITO, "Outline and Problems of Carbon Nano Tube," KINOU ZAIRYOU (Functional Material), vol. 21, No. 5, p. 6-14, May, 2001

Patent Document 1: Japanese Patent National Publication No. 2003-517604

DISCLOSURE OF THE INVENTION

Problems to be Solved by the Invention

As described above, the sensing technique utilizing CNT is promising, for sensing a specific chemical substance serving as a marker in a gas. The technique disclosed in Non-Patent Document 2, however, is considered not having selectivity to the substance as the object of sensing. This was confirmed by an experiment as described in the following.

The inventors of the present invention conducted the following experiment, in order to confirm whether selectivity to a specific chemical substance can be attained by the technique disclosed in Non-Patent Document 2. In the experiment, toluene gas and N2 gas existing in nature are adsorbed by the chemical substance sensing elements in accordance with the technique of Non-Patent Document 2, respectively, and change in electric resistance was measured. As a result, in both samples, there was a difference from when there was no adsorbed gas, and it was confirmed that some substance exists. Significant difference, however, cannot be found between N2 gas and toluene, in the change of electric resistance.

Specifically, the sensor using the technique disclosed in Non-Patent Document 2 is considered to have no selectivity to the substance as the object of sensing. Though it is possible to confirm presence of a substance in the atmosphere, qualitative analysis to know "what the substance is" is impossible. Therefore, as regards the marker detection, it hardly has any utility value.

Further, the sensing technique disclosed in Patent Document 1 does not handle marker monitoring and its performance is unknown.

Therefore, an object of the present invention is to provide a chemical substance sensing element having high performance and marker selectivity to markers included in biological information, manufacturing method thereof, and a chemical substance sensing apparatus using such a chemical substance sensing element.

Another object of the present invention is to provide a chemical substance sensing element including a carbon nanostructure, having high performance and marker selectivity to markers included in biological information, manufacturing method thereof, and a chemical substance sensing apparatus using such a chemical substance sensing element.

Means for Solving the Problems

According to a first aspect, the present invention provides a chemical substance sensing element, including an electrically conductive sensing body surface-modified with metal complex or its derivative, for detecting a specific chemical substance.

Preferably, the sensing body includes a carbon nanostructure.

The chemical substance sensing element includes, as a portion adsorbing the gas as the object of sensing, a carbon nanostructure that can be manufactured easier than CNT. The inventors consider that the technique described in Non-Patent Document 1 is applicable to any carbon nanostructure, not limited to CNT. The reason for this is that the technique described above makes use of conductivity and nanostructure as characteristics of carbon nanostructure. In addition, the present carbon nanostructure has its surface modified by metal complex or its derivative and, from the reason described below, it is believed to have substance selectivity. Specifically, an unmodified carbon nanostructure is in a very stable bonding state and not electrically polarized, whereas a carbon nanostructure modified by metal complex or its derivative has modified groups polarized and because of its electric characteristic, it adsorbs only a specific substance on its surface. Further, at the time of adsorption, a modified structure exhibits a behavior largely reflecting difference in bonding state or charge state resulting from gas types, as compared with an unmodified structure. This influences the change in electric resistance of carbon nanostructure, to attain gas selectivity. Further, modification by metal complex or its derivative improves sensitivity of the chemical substance sensing element formed of a carbon nanostructure. Consider the space structure. The modified structure may be considered to be a carbon nanostructure provided by deforming the graphane sheet as mentioned above having substituent group of metal complex or its derivative added as a side chain, so that there is a space allowing gas adsorption around the substituent group, while in the unmodified structure, there is a structural restriction.

The present chemical substance sensing element is capable of detecting, with high sensitivity, a specific chemical substance included in the biological information that has been difficult to detect by the prior art. Specifically, by the present element, a chemical substance sensing element formed of a carbon nanostructure, having high performance and marker selectivity to markers included in biological information can be provided.

More preferably, the metal complex consists of metal phthalocyanines.

The chemical substance sensing element includes, as the portion adsorbing the gas as the object of sensing, a carbon nanostructure having its surface modified by metal phthalocyanine. Metal phthalocyanine is a complex of cyclic compound phthalocyanine (phtalocyanine or tetrabenzoazaporphyrin, $C_{32}N_8H_{16}$) having four phthalic imides cross-linked by nitrogen atom, and a metal arranged at the central portion thereof. The inventors have found through simulation based on density functional theory (hereinafter referred to as "DFT") that a carbon nanostructure modified by metal phthalocyanine (hereinafter referred to as "MePc") has higher adsorption capability for pentane than an unmodified structure. Pentane is a marker related to oxidative stress-induced disease in the expired gas. In addition, by modifying its surface with MePc, the sensitivity can be improved from the following reason. For sensing with the chemical substance sensing element, an electric field is applied to measure the change in electric resistance. Therefore, electrons move inside the carbon nanostructure. When electrons move and enter MePc that are added to the surface of carbon nanostructure because of the modification, excited state is attained, whereby metal is oxidized and charged with positive charges while phtalocyanine is further charged with negative charges, to be more active to adsorption of the substance. If reaction with the specific chemical substance occurs, resulting change in electric characteristic is transmitted at high speed to the carbon nanostructure through Π electron bonding commonly held in the entire molecular structure of each carbon nanostructure and MePc, so that the change in electric resistance occurs quickly.

Specifically, by the present element, a chemical substance sensing element formed of a carbon nanostructure, having marker selectivity and higher sensitivity than the prior art to markers included in biological information can be provided.

More preferably, in the chemical substance sensing element, the specific chemical substance to be detected is selected from the group consisting of nitric oxide (hereinafter denoted as "NO") and pentane.

The inventors confirmed that the chemical substance sensing element including the carbon nanostructure surface-modified with MePc in accordance with the present invention detects NO and pentane with high sensitivity. This is because MePc has high adsorption capability to NO and pentane due to its electric characteristic. NO and pentane are known as markers in expired gas. NO relates to pulmonary disease and pentane relates to oxidant stress.

Specifically, by the present element, a chemical substance sensing element having selectivity and higher sensitivity than the prior art to nitric oxide and pentane as marker substances included in biological information can be provided.

According to a second aspect, the present invention provides a chemical substance sensing element, including a sensing body surface-modified with a fluorescent molecule, which is capable of selective bonding to the specific chemical substance and whose product of bonding generates fluorescence of a specific wavelength upon irradiation with excitation light, for detecting a specific chemical substance.

Preferably, the sensing body includes a carbon nanostructure.

The present chemical substance sensing element includes, as a portion adsorbing the gas as the object of sensing, a carbon nanostructure with its surface modified by a fluorescent molecule. Further, the fluorescent molecule selectively bonds to the specific chemical substance as a marker, because of its molecular structure and electric characteristic. When the product resulting from the bonding is irradiated with light of a specific wavelength, the product is excited and generates fluorescence of a specific wavelength. Therefore, by measuring the fluorescence excitation reaction of the present chemical substance sensing element, presence of the specific chemical substance in the gas as the object of measurement can be confirmed. Further, even when the gas as the object of measurement contains a plurality of components, sensing of individual marker is possible, because of reaction selectivity of the fluorescent molecule.

Specifically, by the present invention, a chemical substance sensing element formed of a carbon nanostructure, having high selectivity and high sensitivity to markers included in biological information can be provided.

More preferably, the fluorescent molecule is diaminofluorescein-2 (hereinafter referred to as "DAF-2").

More preferably, the specific chemical substance to be detected by the chemical substance sensing element is NO.

Amino group included in the molecular structure of DAF-2 reacts with nitric oxide, and forms diaminofluorescein-2-triazole (hereinafter referred to as "DAF-2T"). When DAF-2T is irradiated with excitation light having the wavelength of 495 nm, fluorescence with the wavelength of 515 nm generates. This can be used for confirming presence/absence of nitric oxide in the biological information.

The inventors confirmed that the chemical substance sensing element including the carbon nanostructure surface-modified with DAF-2 can detect NO in the gas as the object of measurement and that it has high sensitivity with the detection lower limit being 100 ppb or lower.

By the present invention, a chemical substance sensing element capable of monitoring NO with higher sensitivity than the prior art can be provided.

Preferably, the fluorescent molecule included in the chemical substance sensing element is 2,4-dinitrophenylhydrazine (hereinafter referred to as "DNPH").

More preferably, in the chemical substance sensing element, the specific chemical substance to be detected is acetone.

Terminal amino group of DNPH reacts with acetone and generates imine. When the product is irradiated with excitation light having the wavelength of 440 nm, again, fluorescence of a specific wavelength is observed. Thus, it is possible to confirm presence/absence of acetone in the biological information.

The inventors confirmed that the chemical substance sensing element including carbon nanostructure surface-modified with DNPH can detect acetone in the gas as the object of sensing, and that it has high sensitivity with the detection lower limit being 100 ppb or lower.

By the present invention, a chemical substance sensing element capable of monitoring acetone with higher sensitivity than the prior art can be provided.

According to a third aspect, the present invention provides a chemical substance sensing element, including an electrically conductive sensing body surface-modified with metal complex or its derivative and a fluorescent molecule, for detecting a specific chemical substance. The fluorescent molecule included in the present element is capable of selective bonding to the specific chemical substance and product of bonding generates fluorescence of a specific wavelength upon irradiation with excitation light.

Preferably, the sensing body includes a carbon nanostructure.

More preferably, the metal complex consists of MePcs.

More preferably, the fluorescent molecule is DAF-2.

In the carbon nanostructure surface-modified with MePc as a metal complex and DAF-2 as a fluorescent molecule, specific chemical substances react with MePc and DAF-2 and reaction products generate, respectively. Therefore, when the gas as the object of measurement is introduced to the present element and fluorescence excitation reaction and change in electric resistance caused by adsorption of specific chemical substances to the element are measured simultaneously, the number of different types of specific chemical substances detectable at one time can be increased, and a specific chemical substance that cannot be detected because of, for example, insufficient sensitivity in one measurement method can be detected complimentarily by the other measurement method.

According to a fourth aspect, the present invention provides a chemical substance sensing element for detecting a specific chemical substance, including: a first sensing element including a first sensing body surface-modified with a first fluorescent molecule; and a second sensing element including a second sensing body surface-modified with a second fluorescent molecule different from the first fluorescent molecule.

Preferably, the first and second sensing bodies both include carbon nanostructures.

Since first and second sensing elements including carbon nanostructures respectively surface-modified with first and second fluorescent molecules are used, it is possible to separately detect different chemical substances by these sensing elements. Therefore, a chemical substance sensing element capable of simultaneously and separately detecting a plurality of chemical substances in the biological information can be provided.

More preferably, the first and the second fluorescent molecules are selected from the group consisting of DAF-2 and DNPH.

The first and the second sensing elements including carbon nanostructures, respectively surface-modified with DAF-2 and DNPH, are used. Therefore, even when the biological information contains a number of different types of chemical substances, it is possible to simultaneously and separately detect nitric oxide, for example, by the first sensing element and acetone, for example, by the second sensing element.

According to a fifth aspect, the present invention provides a chemical substance sensing apparatus, including: a chemical substance sensing element including an electrically conductive sensing body surface-modified with a metal complex or its derivative; and detecting means, electrically connected to the chemical substance sensing element, for detecting a change in electric resistance of the chemical substance sensing element.

Preferably, the sensing body in the chemical substance sensing apparatus includes a carbon nanostructure.

More preferably, the metal complex modifying the surface of sensing body consists of MePc.

According to the present apparatus, it is possible to sense a chemical substance with selectivity to a specific chemical substance included in the biological information and higher sensitivity than the prior art.

More preferably, the chemical substance sensing apparatus further includes means for heating, for irradiating with light or for evacuating the chemical substance sensing element, whereby substance adsorbed on a surface of the chemical substance sensing element is substantially removed.

By the present apparatus, it is possible to remove the substance adsorbed to the surface of chemical substance sensing element, allowing re-use.

According to a sixth aspect, the present invention provides a chemical substance sensing apparatus, including: a chemical substance sensing element including a sensing body surface-modified with a fluorescent molecule, which is capable of selective bonding to the specific chemical substance and whose product of bonding generates fluorescence of a specific wavelength upon irradiation with excitation light; a fluorescence detector arranged to allow detection of fluorescence generated by the excitation light from the fluorescent molecule bonded to the chemical substance sensing element; and a determining device, connected to the fluorescence detector, for determining presence/absence of the fluorescence of the specific wavelength.

Preferably, the chemical substance sensing apparatus further includes a light emitter arranged at a position allowing, with light emitted therefrom, irradiation of the chemical substance sensing element, for emitting excitation light to the fluorescent molecule.

More preferably, the sensing body in the chemical substance sensing apparatus includes a carbon nanostructure.

More preferably, the fluorescent molecule modifying the surface of sensing body is selected from the group consisting of DAF-2 and DNPH.

According to the present apparatus, it is possible to sense a chemical substance with selectivity to a specific chemical substance included in the biological information and higher sensitivity than the prior art.

Preferably, the chemical substance sensing apparatus further includes a device for heating, for irradiating with light or for evacuating the chemical substance sensing element, whereby substance adsorbed on a surface of the chemical substance sensing element is substantially removed.

By the present apparatus, it is possible to remove the substance adsorbed to the surface of chemical substance sensing element, allowing re-use of the chemical substance sensing element.

According to a seventh aspect, the present invention provides a chemical substance sensing apparatus, including: a chemical substance sensing element for detecting a specific chemical substance, including an electrically conductive sensing body surface-modified with metal complex or its derivative and a fluorescent molecule; a detector, electrically connected to the chemical substance sensing element, for detecting a change in electric resistance of the chemical substance sensing element; a fluorescence detector arranged to allow detection of fluorescence generated by excitation light from the fluorescent molecule bonded to the chemical substance sensing element; and a determining device, connected to the fluorescence detector, for determining presence/absence of fluorescence of a specific wavelength. The fluorescent molecule included in the apparatus is capable of selective bonding to the specific chemical substance and product of bonding generates fluorescence of a specific wavelength upon irradiation with the excitation light.

Preferably, the chemical substance sensing apparatus further includes a light emitter arranged at a position allowing, with light emitted therefrom, irradiation of the chemical substance sensing element, for emitting the excitation light to the fluorescent molecule.

More preferably, the sensing body includes a carbon nanostructure.

More preferably, the metal complex consists of MePcs.

The fluorescent molecule may be DAF-2.

In the carbon nanostructure surface-modified with MePc as a metal complex and DAF-2 as a fluorescent molecule, specific chemical substances react with MePc and DAF-2 and reaction products generate, respectively. Therefore, when the gas as the object of measurement is introduced to the present apparatus and fluorescence excitation reaction and change in electric resistance caused by adsorption of specific chemical substances to the chemical substance sensing element are measured simultaneously, the number of different types of specific chemical substances detectable at one time can be increased, and a specific chemical substance that cannot be detected because of, for example, insufficient sensitivity in one measurement method can be detected complimentarily by the other measurement method.

The chemical substance sensing apparatus further includes a device for heating, for irradiating with light or for evacuating the chemical substance sensing element, whereby substance adsorbed on a surface of the chemical substance sensing element is substantially removed.

By the present apparatus, it is possible to remove the substance adsorbed to the surface of chemical substance sensing element, allowing re-use of the chemical substance sensing element.

According to an eighth aspect, the present invention provides a chemical substance sensing apparatus, for detecting a specific chemical substance, including: a first chemical substance sensing element including an electrically conductive sensing body surface-modified with a metal complex or its derivative; a second chemical substance sensing element including an electrically conductive sensing body surface-modified with a fluorescent molecule; a detector, electrically connected to the first chemical substance sensing element, for detecting a change in electric resistance of the first chemical substance sensing element; a fluorescence detector arranged to allow detection of fluorescence generated by excitation light from the fluorescent molecule bonded to the second chemical substance sensing element; and a determining device, connected to the fluorescence detecting means, for determining presence/absence of fluorescence of a specific wavelength. The fluorescent molecule is capable of selective bonding to the specific chemical substance and product of bonding generates fluorescence of the specific wavelength upon irradiation with the excitation light.

Preferably, the chemical substance sensing apparatus further includes a light emitter, arranged at a position allowing, with light emitted therefrom, irradiation of the second chemical substance sensing element, for emitting the excitation light to the fluorescent molecule.

More preferably, the sensing body includes a carbon nanostructure.

More preferably, the metal complex consists of MePcs.

The fluorescent molecule may be DAF-2.

In the carbon nanostructure surface-modified with MePc as a metal complex and the carbon nanostructure surface-modified with DAF-2 as a fluorescent molecule, specific chemical substances react with MePc and DAF-2 and reaction products generate, respectively. Therefore, when the gas as the object of measurement is introduced to the present apparatus and fluorescence excitation reaction and change in electric resistance caused by adsorption of specific chemical substances to the element are measured simultaneously, the number of different types of specific chemical substances detectable at one time can be increased, and a specific chemical substance that cannot be detected because of, for example, insufficient sensitivity in one measurement method can be detected complimentarily by the other measurement method.

The chemical substance sensing apparatus further includes a device for heating, for irradiating with light or for evacuating the chemical substance sensing element, whereby substance adsorbed on a surface of the chemical substance sensing element is substantially removed.

By the present apparatus, it is possible to remove the substance adsorbed to the surface of chemical substance sensing element, allowing re-use of the chemical substance sensing element.

According to a ninth aspect, the present invention provides a method of manufacturing a chemical substance sensing element for detecting a specific chemical substance, including the steps of: fabricating an electrically conductive sensing body on a plane; dripping a solution containing metal complex or its derivative and a fluorescent molecule to the fabricated sensing body; and applying a prescribed voltage between the sensing body and another portion in an area where the solution containing the fluorescent molecule was dripped on the sensing body on the plane. The fluorescent molecule is capable of selective bonding to the specific chemical substance and product of bonding generates fluorescence of a specific wavelength upon irradiation with excitation light. By the method, a surface of the sensing body is substantially uniformly modified with the metal complex or its derivative and the fluorescent molecule.

Preferably, the electrically conductive sensing body includes a carbon nanostructure.

Effects of the Invention

As described above, according to the present invention, a chemical substance sensing element having a sensing body preferably formed of carbon nanostructure, having marker selectivity and high sensitivity for sensing a specific substance included in biological information, which has been difficult to attain in the prior art, can be provided. This element is capable of marker-selective sensing of chemical substance, including NO, pentane and acetone. In addition, as the higher sensitivity can be attained by surface processing, it becomes possible to sense a small amount of marker, of which detection has been difficult to date.

BRIEF DESCRIPTION OF THE DRAWINGS

FIG. 5 is an illustration related to the structure and operation of a chemical substance sensing unit in accordance with the second embodiment.

FIG. 7 shows a structure of a chemical substance sensing element 128 in accordance with a fourth embodiment.

FIG. 8 shows a structure of a chemical substance sensing element 142 in accordance with a fifth embodiment.

FIG. 11 shows a result of measurement of Example 1 in accordance with the first embodiment.

Figure 1:
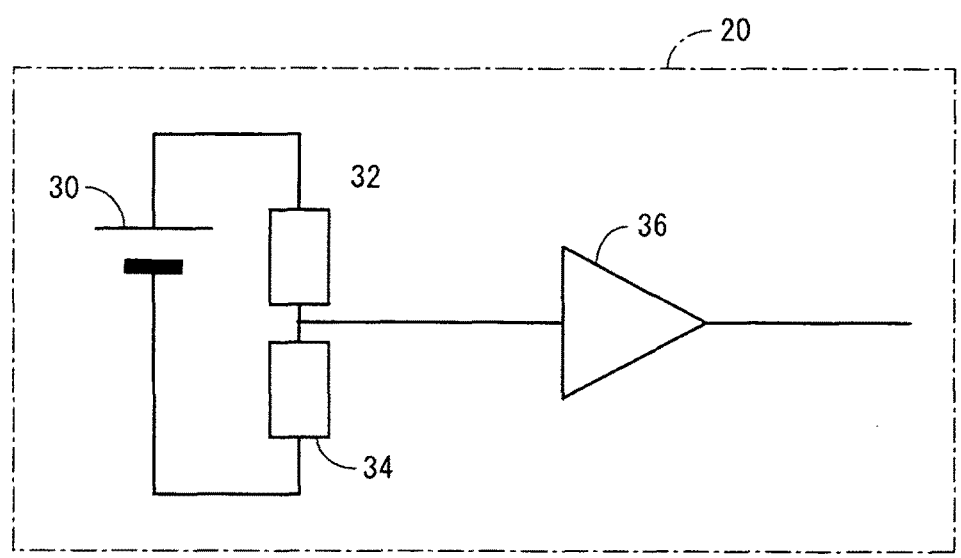
FIG. 1 shows a configuration of a chemical substance sensing apparatus 20.

DESCRIPTION OF THE REFERENCE SIGNS 20, 62 chemical substance sensing apparatuses, 30, 192 DC power sources, 32, 108, 128, 142, 180, 200, 210, 270 chemical substance sensing elements, 34 load resistance, 36 amplifier, 40a, 40b electrodes, 42, 66 chemical substance sensing units, 50, 80 CNTs, 52, 82, 84 substances added for modifying CNT surface, 64 container, 67 light source, 68 optical path container, 69 dichroic mirror, 70 CCD camera, 71 display system, 72, 100 excitation lights, 73, 102, 124, 126 fluorescence, 74 display screen, 110 plate, 120, 122 wells on plate for supporting chemical substance sensing unit, 130, 150, 190, 280 substrates, 132, 152, 153, 202, 203, 212, 213 comb-shaped patterns, 138, 178, 179 carbon nanostructure, 139, 140, 154, 156, 204, 206, 214, 216, 286, 288 nodes, 134, 170 solid substrate, 135, 172 thermally oxidized films, 136, 174 buffer layers, 175 opening, 137, 176 catalyst layers, 282 Au electrode for manufacturing chemical substance sensing element, 284 dispersion solution.

BEST MODES FOR CARRYING OUT THE INVENTION

In the following, embodiments of the present invention will be described with reference to the drawings. In the following description and in the drawings, the same parts or components are denoted by the same reference characters. Their functions are also the same. Therefore, detailed description thereof will not be repeated.

[First Embodiment]—Structure—

FIG. 1 shows a configuration of a chemical substance sensing apparatus 20 using the chemical substance sensing element in accordance with a first embodiment of the present invention. Referring to FIG. 1, apparatus 20 includes a DC power source 30, a chemical substance sensing element 32 in accordance with the present embodiment, having one end connected to a plus terminal of DC power source 30, a load resistance 34 connected between the other end of chemical substance sensing element 32 and a minus terminal of DC power source 30, and an amplifier 36 having an input connected to a node between chemical substance sensing element 32 and load resistance 34 for amplifying potential change at this node. At the time of measurement, in order to measure the potential change, a DC voltmeter, not shown, is connected to the other terminal of amplifier 36.

Figure 2:
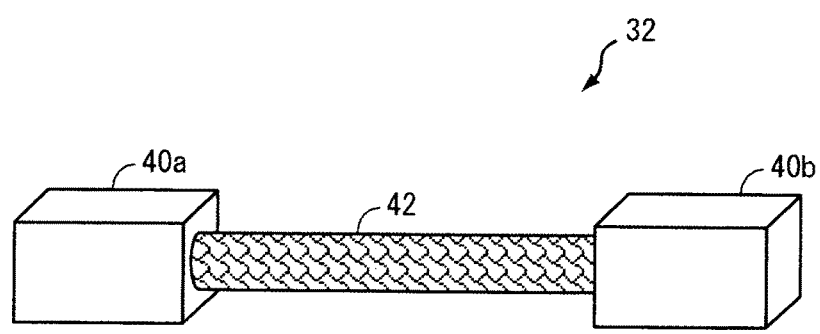
FIG. 2 shows a structure of a chemical substance sensing element 32 in accordance with a first embodiment of the present invention.

FIG. 2 shows a structure of chemical substance sensing element 32. Referring to FIG. 2(A), chemical substance sensing element 32 includes a chemical substance sensing unit 42 formed of a carbon nanostructure with its surface modified by metal complex MePc, serving as a sensing body, and electrodes 40a and 40b arranged at opposite ends of chemical substance sensing unit 42 and electrically connected to chemical substance sensing unit 42.

Figure 3:
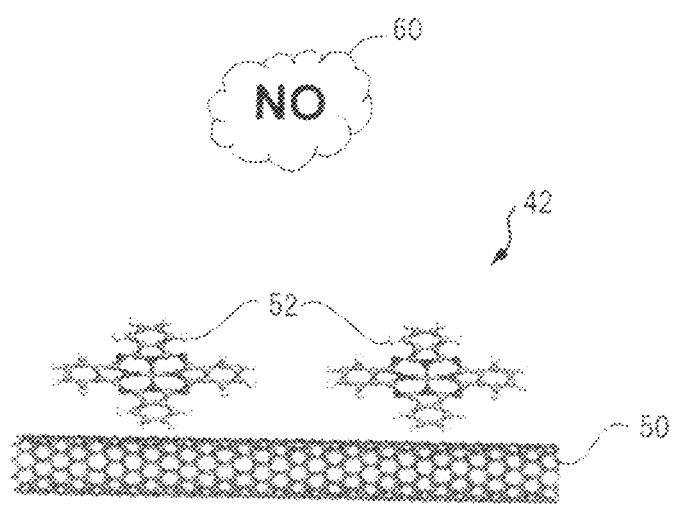
FIG. 3 is an illustration related to the structure and operation of a chemical substance sensing unit 42 in accordance with the first embodiment.

Chemical substance sensing unit 42 is formed of an aggregate of carbon nanostructures such as carbon nano tubes, carbon nano fibers or fullerene. Therefore, chemical substance sensing unit 42 contains a large number of CNT and the like. FIG. 3 is a conceptual illustration of one CNT 50 included in chemical substance sensing unit 42. Referring to FIG. 3, in the present embodiment, MePc molecules 52 are applied to the surface of CNT 50. Other carbon nano tubes (and therefore, chemical substance sensing unit 42 also) are also surface-modified with MePc.

MePc has selective ability of reacting with only a specific substance. Resistance value of chemical substance sensing unit 42 when electric current is caused to flow through chemical substance sensing unit 42 formed of MePc-modified carbon nanostructure changes depending on whether or not a substance is adsorbed on chemical substance sensing unit 42. Since chemical substance sensing unit 42 adsorbs a specific substance in the atmosphere, the manner of change in its electric resistance differs depending on whether or not the specific substance exists in the atmosphere. Therefore, by the apparatus shown in FIG. 1, a specific substance in the atmosphere can selectively be detected. Specifically, by introducing expired gas to apparatus 20 and measuring an output of DC voltmeter, a specific substance in the expired gas can selectively be detected.

—Method of Manufacturing Chemical Substance Sensing Element 32—

Chemical substance sensing element 32 is manufactured in the following manner. The carbon nanostructure forming the sensing body may be produced using a conventional method. After producing carbon nanostructure, refluxing process is conducted to remove impurities. Thereafter, the resulting body is dried and put in an MePc solution, and ultrasonic wave is applied, whereby a dispersion liquid having carbon nanostructures uniformly dispersed in MePc solution is produced. Thereafter, the resulting body is dried to provide chemical substance sensing unit 42, and electrodes are attached to opposite ends thereof. Thus, chemical substance sensing element 32 is completed.

—Operation—

Referring to FIGS. 1, 2 and 3, apparatus 20 in accordance with the present invention operates in the following manner. Referring to FIG. 1, the gas as an object of measurement is introduced to the surface of chemical substance sensing element 32, while a constant voltage is applied across opposite ends of series connection of chemical substance sensing element 32 and load resistance 34 from DC power source 30.

Referring to FIG. 2, when a chemical substance in the gas as the object of measurement adheres to the surface of carbon nanostructure forming chemical substance sensing unit 42 included in chemical substance sensing element 32, electric resistance between electrodes 40a and 40b changes. The change is detected by a DC voltmeter, not shown, as a change in output voltage from amplifier 36.

FIG. 3 illustrates NO adhering to a surface of CNT 50 having its surface modified with MePc. As described above, since MePc has selectivity to substance it adsorbs, NO 60 is adsorbed. Each of CNTs 50 and other carbon nanostructures forming chemical substance sensing unit 42 adsorbs the substance, and total sum of changes in electric resistance is detected as the change in output voltage of apparatus 20 shown in FIG. 1.

The reason for this is as follows. In chemical substance sensing unit 42, each nanostructure is in contact with a neighboring nanostructure. Therefore, when viewed as a whole, chemical substance sensing unit 42 is an electrically conductive aggregate. As described above, electric resistance across opposite ends of the aggregate changes when any substance adheres to the surface of nanostructure. Therefore, by checking the change in electric resistance across opposite ends of chemical substance sensing unit, it is possible to know that some substance adheres to chemical substance sensing unit 42 and, therefore, to know that some substance exists in the atmosphere.

In addition, MePc modifying the surface of chemical substance sensing unit 42 selectively adsorbs a specific substance. Therefore, from the amount of change in electric resistance of chemical substance sensing unit 42 as a whole, it is possible to confirm presence/absence of the specific substance in the biological information.

It is noted that MePc has adsorption selectivity to pentane. Table 2 shows pentane adsorption energy of MePcs of different coordination metals and of CNT as a representative of carbon nanostructure, calculated using a DFT-based simulator (Dmol$^3$, manufactured by Accelrys). Since all MePc examples have adsorption energy lower than CNT, it can be expected that they have higher adsorption ability to pentane than CNT. Therefore, pentane adsorption ability of MePc is estimated to be higher than that of carbon nanostructure.

TABLE 2

| Surface modification | Target | Adsorption energy (eV) | Electronegativity |
|---|---|---|---|
| CuPc | Pentane | −0.03570952 | Cu: 1.90 |
| CoPc | Pentane | −0.046017199 | Co: 1.88 |
| ZnPc | Pentane | −0.045116501 | Zn: 1.65 |

TABLE 2-continued

| Surface modification | Target | Adsorption energy (eV) | Electronegativity |
|---|---|---|---|
| MnPc | Pentane | −0.048953309 | Mn: 1.55 |
| CNT | Pentane | −0.018724164 | — |

In order to re-use the chemical substance sensing element, it is necessary to remove the previously measured gas as the object of measurement. Here, the adsorbed gas as the object of measurement can be desorbed by increasing temperature of chemical substance sensing element 32. Various means may be provided for increasing the temperature of chemical substance sensing element 32. In apparatus 20 in accordance with the present embodiment, at the time of gas desorption process, the voltage of DC power source 30 is adjusted to be high so that the temperature of chemical substance sensing element 32 is increased to about 200° C., whereby various substances as the objects of sensing are removed. Alternatively, means for periodically heating chemical substance sensing element 32 at 150° C. may be provided. Heating by laser beam irradiation using semiconductor laser is also available. The method of desorbing substance as the object of sensing is not limited to the above and, by way of example, evacuation is also possible.

As described above, apparatus 20 in accordance with the present embodiment measures the change in electric resistance of chemical substance sensing unit 42. The manners of change in electric resistance when a specific substance adheres to and does not adhere to chemical substance sensing unit can be distinguished. Therefore, by apparatus 20, it is possible to detect a specific substance in the atmosphere. Since carbon nanostructure is used, the change in electric resistance reflects the amount of adsorbed substance with high sensitivity. Therefore, it is possible to detect the specific chemical substance in the atmosphere with high sensitivity.

Though MePc has been described as an example of metal complex, it is not limiting and, generally, effects similar to those of the embodiment above can be attained by using a metal complex or its derivative.

In the embodiments below, parts of the structure, operations and the principle of substance detection are the same as those of the first embodiment. Therefore, in the following description of embodiments, details thereof will not be repeated.

[Second Embodiment]

In the chemical substance sensing in accordance with the present embodiment, a carbon nanostructure having its surface modified with a specific fluorescent molecule is used. As the fluorescent molecule, one that reacts with a specific substance included in the biological information and whose reaction product is excited and generates fluorescence of a prescribed wavelength when irradiated with light of a specific wavelength is used. Specifically, the present embodiment adopts a sensing element using a carbon nanostructure having its surface modified with such a fluorescent molecule.

—Structure—

Figure 4:
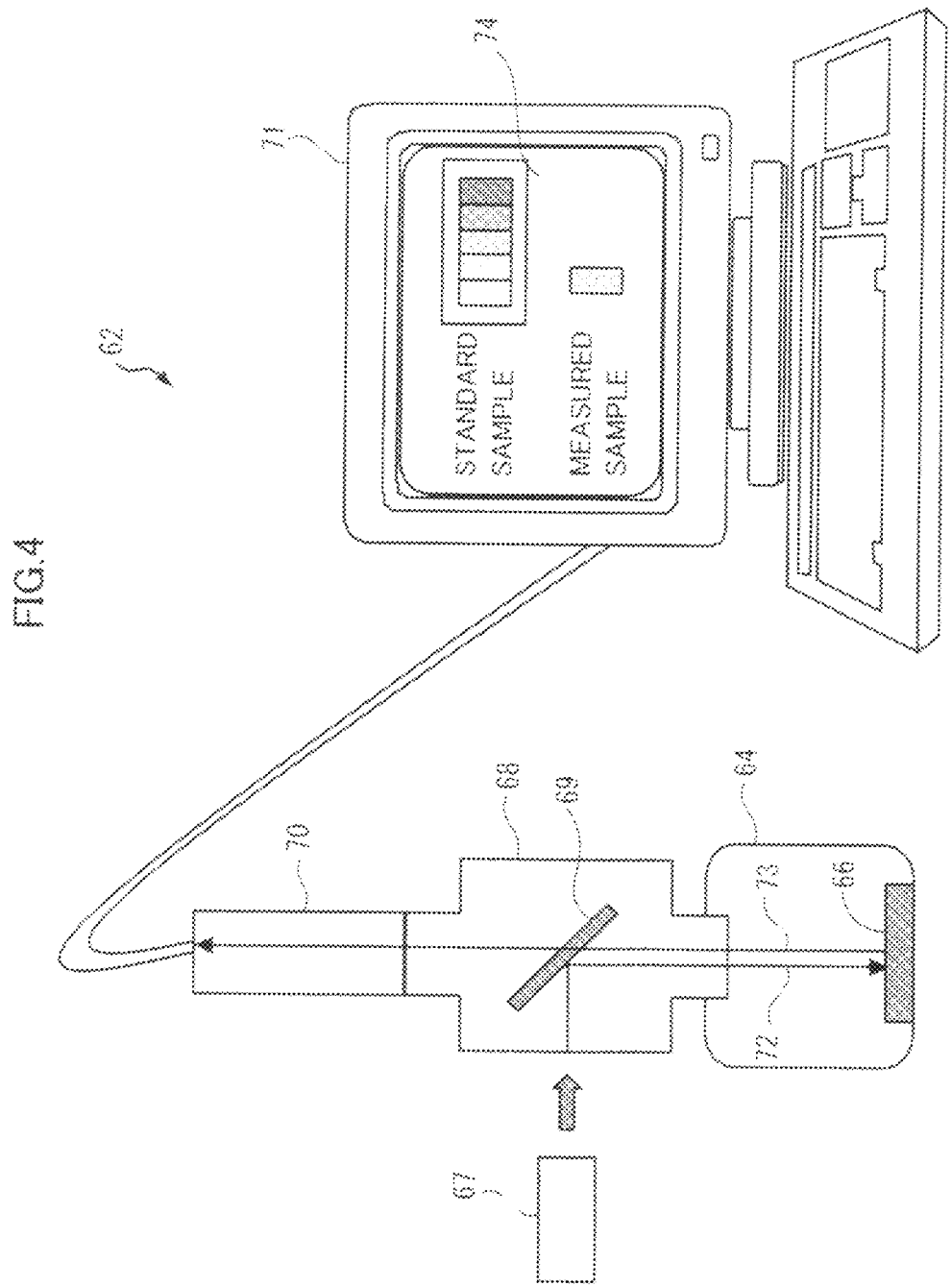
FIG. 4 shows a structure of a chemical substance sensing apparatus 62 in accordance with a second embodiment.

FIG. 4 shows a structure of a chemical substance sensing apparatus 62 adopting the chemical substance sensing element in accordance with the second embodiment. Referring to FIG. 4, apparatus 62 includes: a container 64 for providing a closed system of ambient atmosphere around the sensing element, to enable gas sensing free from the influence of air; a chemical substance sensing unit 66 placed in container 64; a light source 67 emitting light 72; a dichroic mirror 69 arranged directly above chemical substance sensing unit 66 such that light 72 from light source 67 is reflected to chemical substance sensing unit 66 and fluorescence 73 from chemical substance sensing unit 66 is transmitted; an optical path container 68 connected to container 64, housing dichroic mirror 69 and forming optical paths for light 72 from light source 67 and fluorescence 73 from chemical substance sensing unit 66; a CCD camera 70 provided at a position where fluorescence 73 from chemical substance sensing unit 66 reaches, for picking-up an image obtained by fluorescence 73 generated from chemical substance sensing unit 66; and a display system 71 connected to receive an output of CCD camera 70, for displaying a color of the image formed by fluorescence 73 generated by excitation in comparison with images (colors) obtained from a plurality of standard samples on a display screen 74, thereby allowing confirmation by the user as to the presence/absence of a specific chemical substance.

FIG. 5(A) is a conceptual illustration of one CNT 80 included in the carbon nanostructure in chemical substance sensing unit 66. Referring to FIG. 5(A), to the surface of CNT 80, DAF-2(82), which is a fluorescent molecule, is applied for modification. Other carbon nanostructures (and therefore, chemical substance sensing unit 66) are also similarly modified.

As will be described later, since amino group of DAF-2 reacts with NO and forms triazole, when it receives light of a specific wavelength (495 nm), it generates fluorescence of a specific wavelength (515 nm). Therefore, by the apparatus shown in FIG. 4, NO in biological information can selectively be detected.

—Method of Manufacturing Chemical Substance Sensing Unit 66—

Chemical substance sensing unit 66 is manufactured in the similar manner as chemical substance sensing element 32 in accordance with the first embodiment. It is noted, however, that in place of MePc solution used in the first embodiment, DAF-2 solution is used, to produce a dispersed liquid of carbon nanostructures. Thereafter, it is dried to provide chemical substance sensing unit 66. In the present embodiment, NO is detected using fluorescence, and change in electric resistance is not utilized. Therefore, different from the first embodiment, it is unnecessary to provide electrodes on the carbon nanostructure.

—Operation—

Referring to FIGS. 4 and 5, apparatus 62 in accordance with the present embodiment operates in the following manner. Referring to FIG. 4, chemical substance sensing unit 66 is placed in container 64, and the gas as the object of measurement is introduced to container 64. Here, the gas as the object of measurement is a mixed gas of NO and $O_2$ forming the atmospheric air. As a result, NO is adsorbed by chemical substance sensing unit 66. Its amount has positive correlation with NO concentration in the gas as the object of measurement. Then, excitation light 72 whose wavelength is adjusted to 495 nm is generated from light source 67, which is directed through dichroic mirror 69 to chemical substance sensing unit 66.

Referring to FIG. 5(A), when NO molecule 90 in the gas as the object of measurement comes close to chemical substance sensing unit 66, amino group of DAF-2 82 modifying the surface of CNT 80 reacts with NO to generate triazole, and changes to DAF-2T 84, as shown in FIG. 5(B). When DAF-2T 84 is irradiated with excitation light 100 having the wavelength of 495 nm, it generates green fluorescence having the wavelength of 515 nm.

Again referring to FIG. 4, fluorescence 73 generated from chemical substance sensing unit 66 proceeds radially and a part thereof enters optical path container 68. Fluorescence 73 introduced to optical path container 68 passes through dichroic mirror 69 and proceeds to CCD camera 70, and its image is picked-up by CCD camera 70. The picked-up image is transferred to display system 71, and displayed as an image of measurement sample, together with standard samples, on display screen 74.

Here, by comparing the color of fluorescence from the measured sample with the standard samples, it is possible to confirm presence/absence of NO in the gas as the object of measurement.

Referring to FIG. 5(B), even when NO molecules 90 as the chemical substance to be sensed exist mixed with other gas molecules (for example, $O_2$ molecules 92) forming the atmospheric air, DAF-2 82 does not react therewith and fluorescence excitation does not occur. Therefore, it is possible to detect NO distinguished from $O_2$ or the like in the atmospheric air.

—Modification—

In place of DFA-2, fluorescent molecules listed in Table 3 may be used for modifying the surface of carbon nanostructure, to provide chemical substance sensing unit 66.

TABLE 3

| Fluorescent molecule | | Excitation wavelength | Fluorescence wavelength | Substance as detection object |
|---|---|---|---|---|
| DAF-2 | Diaminofluorescein-2 (C20H14N2O5) | 495 | 515 | NO |
| DAR | Diaminorhodamine (C26H29N4O4−) | 560 | 575 | NO |
| DAC | Diaminocyanine (C36H38N4OR2 + X−) | 750 | 790 | NO |
| CuFL | Cu(II) fluorescein-based NO probe | 503 | 520 | NO |
| DAN | 2,3-Diaminonaphthalene (C10N10N2) | 365 | 450 | NO2— (derived from NH3) |

[Third Embodiment]

In chemical substance sensing in accordance with the present embodiment, as in the second embodiment, specific chemical substance is sensed utilizing fluorescence excitation and, using a microplate, it is made possible to confirm, by measurement at one time, presence/absence of a plurality of chemical substances as the object of sensing.

—Structure—

The chemical substance sensing apparatus adopting the chemical substance sensing element in accordance with the third embodiment has a structure similar to the chemical substance sensing apparatus 62 in accordance with the second embodiment shown in FIG. 4. It is noted, however, that it includes a chemical substance sensing element for sensing a plurality of chemical substances, in place of chemical substance sensing unit 66.

FIG. 6(A) is a schematic illustration of chemical substance sensing element 108 for sensing a plurality of chemical substances. Referring to FIG. 6(A), chemical substance sensing element 108 in accordance with the present embodiment includes a substrate plate 110, and a plurality of wells 120, 122 . . . , arranged on plate 110. Wells 120 and 122 respectively detect different chemical substances in the gas as the object of measurement by fluorescence excitation. By way of example, well 120 detects NO and well 122 detects acetone. As the excitation light, ultra violet (hereinafter referred to as "UV") having the wavelength of 200 nm to 800 nm is used, to cover different types of fluorescent substances.

—Method of Manufacturing Chemical Substance Sensing Element 108—

Well 120 for detecting NO and well 122 for detecting acetone shown in FIG. 5 are formed in the following manner.

In well 120, a chemical substance sensing unit formed of a carbon nanostructure surface-modified with DAF-2 in accordance with the second embodiment is mounted.

In well 122, a carbon nanostructure surface-modified with DNPH is mounted as the chemical substance sensing unit.

The method of manufacturing carbon nanostructure required for well 122 is the same as the method of manufacturing carbon nanostructure in accordance with the first embodiment. It is noted, however, that in place of MePc solution used in the first embodiment, a dispersion liquid having carbon nanostructures dispersed uniformly in DNPH solution is prepared and then dried, to provide the chemical substance sensing unit.

—Operation—

Referring to FIGS. 4, 6(A) and 6(B), an operation of the apparatus in accordance with the present embodiment will be described. Referring to FIGS. 4 and 6(A), in chemical substance sensing apparatus 62 shown in FIG. 4, chemical substance sensing element 108 is arranged in container 64, in place of chemical substance sensing unit 66. To container 64, a gas as an object of measurement containing NO and acetone is introduced. Thus, NO and acetone in the gas as the object of measurement is brought to the surface of chemical substance sensing element 108. These are bonded to chemical substance sensing units provided in wells 120 and 122, respectively. Thereafter, UV light having the wavelength of 200 nm to 800 nm is directed as excitation light 72, to chemical substance sensing element 108.

Referring to FIG. 6(B), as a result, well 120 generates green fluorescence 124 having the wavelength of 515 nm when excitation light 72 has the wavelength of 495 nm, and well 122 generates yellowish orange fluorescence 126 when excitation light 72 has the wavelength of 440 nm.

Referring to FIG. 4, images formed by such fluorescence are picked-up by CCD camera 70, detected by display system 71, and based on presence/absence of fluorescence 124 and fluorescence 126 of prescribed wavelengths respectively, presence/absence of NO and acetone in the gas as the object of measurement can be confirmed.

By using chemical substance sensing element 108 as such, it is possible to selectively sense a plurality of specific chemical substances in the gas as the object of measurement.

[Fourth Embodiment]

In the present embodiment, the chemical substance sensing unit for adsorbing the gas as the object of measurement is formed as a sheet, of which shape is patterned, so that the shape of chemical substance sensing unit is optimized for the intended use.

—Structure—

The chemical substance sensing apparatus in accordance with the present embodiment has a structure similar to that of chemical substance sensing apparatus 20 in accordance with the first embodiment. It is noted, however, that in place of chemical substance sensing element 32 shown in FIG. 1, it uses a chemical substance sensing element having a chemical substance sensing unit formed as a sheet pattern.

FIG. 7(A) is a bird's eye view and FIG. 7(B) is a plan view of a chemical substance sensing element 128 used in the present embodiment. FIG. 7(C) is a cross-sectional view in the direction of the arrows along the line C-C of FIG. 7(B).

Referring to FIGS. 7(A) to 7(C), chemical substance sensing element 128 has a plate-shaped substrate 130 having a thermally oxidized film formed on its surface, and a comb pattern 132 including carbon nanostructures fabricated on the surface.

Referring to FIG. 7(C), substrate 130 includes a solid substrate 134 and a thermally oxidized film 135 formed on a surface of solid substrate 134.

Comb pattern 132 includes a buffer layer 136 fabricated as a comb-shape pattern on thermally oxidized film 135, a metal catalyst layer 137 formed on buffer layer 136, and a number of carbon nanostructures 138 formed erected vertically on the surface of metal catalyst layer 137. Buffer layer 136 is formed of an insulator.

Chemical substance sensing element 128 is arranged such that a node 139 as one of the opposite ends of the comb is connected to a plus terminal of a DC current such as DC power source 30 shown in FIG. 2 and a node 140 as the other end is connected to a load resistance 34. Nodes 139 and 140 are positioned to be connected to a layer of carbon nanostructures 138 shown in FIG. 7(C).

—Method of Manufacturing Chemical Substance Sensing Element 128—

Referring to FIG. 7(C), chemical substance sensing element 128 is manufactured in the following manner. First, substrate 130 is prepared by forming thermally oxidized film 135 on solid substrate 134. Thermally oxidized film 135 is an insulator. In order to have carbon nanostructures grow on substrate 130, a mask in accordance with a pattern is formed on a surface of thermally oxidized film 135, and buffer layer 136 is formed on thermally oxidized film 135.

The carbon nanostructures constituting the chemical substance sensing unit may be produced by a conventional method, in which a catalyst for forming CNT is vapor-deposited on the solid substrate with a metal mask interposed, and carbon nanostructures are produced on the resulting pattern. At this time, it is necessary that diameter of CNT growing catalyst particle can accurately be controlled in the order of nano meter. This is because the diameter of CNT grows in correlation with the diameter of seed catalyst particles.

Next, after forming buffer layer 136, metal catalyst layer 137 is formed using the same mask pattern. After forming catalyst layer 137, carbon nanostructures 138 are fabricated on the surface of catalyst layer 137 using the same mask pattern. Finally, the mask pattern is removed.

Next, referring to FIG. 7(A), node 139 is connected to a plus terminal of a DC power source, not shown, and node 140 is connected to a minus terminal of the DC power source, respectively. Thereafter, a mixture of MePc solution and DAF-2 solution is dripped from directly above substrate 130 using a pipette or the like, to the surface of carbon nanostructures 138, as shown in FIG. 7(C). At this time, carbon nanostructures 138 grow dense in a vertical direction to the surface of catalyst layer 137 as shown in FIG. 7(C) and, therefore, they come to have a filter function. Thus, the mixture of MePc solution and DAF-2 solution is trapped with high efficiency by carbon nanostructures 138.

Thereafter, a voltage from the DC power source is applied to chemical substance sensing element 128, and hence the voltage is applied to carbon nanostructure. Then, surfaces of carbon nanostructures are uniformly modified by MePc and DAF-2. The reason is as follows. As described above, carbon nanostructures 138 grow in the direction vertical to the surface of metal catalyst layer 137 as shown in FIG. 7(C), and the structures are in contact with each other. Further, as mentioned above, carbon nanostructures are good conductor. Therefore, when a voltage is applied to chemical substance sensing element 128 while it is electrically connected in the manner as described above, a current flows through the comb pattern. On the other hand, MePc and DAF-2 as fluorescent molecules have polarities because of their molecular structures and, under electric field, they are drawn to the carbon nanostructures and modify the surfaces.

After surface modification, referring to FIG. 1, chemical substance sensing element 128 in accordance with the present embodiment is introduced to apparatus 20, in place of chemical substance sensing element 32 shown in FIG. 1.

—Operation—

Referring to FIG. 7(C), catalyst layer 137 is inherently formed of metal, which is a conductor, and, therefore, in the present structure, it is expected that change in electric resistance of carbon nanostructures 138 cannot be measured. The reason is as follows. Referring to FIGS. 7(A) and (B), in chemical substance sensing element 128, the electric field is applied between nodes 139 and 140 through carbon nanostructures 138. Here, referring to FIG. 7(C), no current flows through thermally oxidized film 135, solid substrate 134 arranged therebelow and buffer layer 136 as an insulating film, while a current flows through carbon nanostructures 138 and, in addition, metal catalyst layer 137 as a conductor. The inventors, however, have found that catalyst layer 137 formed by an arc plasma gun (hereinafter denoted as "APG") shows insulating characteristic, in the present embodiment. Possible reason may be resistance between fine particles of catalyst metal. Further, the inventors further confirmed that when carbon nanostructures 138 are grown vertically in high density of about $10^{10}$ to $10^{13}/cm^2$ and an electric field is applied in the horizontal direction, they exhibit conductivity. The reason may be that carbon nanostructures 138 come to have higher conductivity because of tunneling effect. From these characteristics, when element 128 is introduced to apparatus 20 shown in FIG. 1 and the change in electric resistance is measured, a current flows through carbon nanostructures 138 shown in FIG. 7(C), and the change in electric resistance can be measured. Thus, it is possible to sense a specific chemical substance.

According to the fourth embodiment, it is possible to arrange a large number of carbon nanostructures on a small area. As a result, amount of specific chemical substance as the object of measurement increases and the change in electric resistance of comb pattern 132 increases. Therefore, the sensitivity of sensing the chemical substance can effectively be improved.

—Modification—

Referring to FIG. 1, the chemical substance sensing element in accordance with the present embodiment may be introduced to apparatus 20 in place of chemical substance sensing element 32, the apparatus 20 may be introduced to container 64 shown in FIG. 4 and arranged in container 64 in place of chemical substance sensing unit 66, and by applying a voltage to the chemical substance sensing element manufactured in the manner as described above using DC power source 30 and by directing excitation light 72, fluorescence excitation reaction and the change in electric resistance can simultaneously be measured. Thus, it is possible to measure a specific chemical substance that reacts with the fluorescent molecule and a specific chemical substance that reacts with MePc.

Further, when carbon nanostructures are formed, as the solid substrate, at least one of substrates including silicon substrate, quartz substrate, compound semiconductor substrate, graphite substrate, Al substrate, Cu substrate, Ag substrate, Au substrate, Fe substrate, Ni substrate, Co substrate, glass substrate, ceramic substrate and polymer substrate, metal oxide materials including $Al_2O_3$, $TiO_2$, $ZrO_2$, $Nb_2O_5$, $SnO_2$, $HfO_2$ and $AlPO_4$, a silicate material including $SiO_2.Al_2O_3$, $SiO_2.TiO_2$, $SiO_2.V_2O_5$, $SiO_2.B_2O_3$ and $SiO_2.Fe_2O_3$, metal material including Pt, Ag and Au, semiconductor material including Si, carbon based material including activated carbon and organic polymer, biomaterials including diatom earth and scallop shells and porous substrate including $SiO_2$, may be used.

Further, as the material forming catalyst particles, by way of example, at least one metal selected from the group consisting of Fe, Ni, Co, Cr, Mo, W, Ti, Au, Ag, Cu, Pt, Ta, Al, Pd, Gd, Sm, Nd and Dy or an alloy thereof may be used.

Further, as a method of applying catalyst, arc plasma method, sputtering, electron beam evaporation, resistive heating, spin coating or the like may be used.

[Fifth Embodiment]

—Structure—

The chemical substance sensing element in accordance with the present embodiment has a structure similar to chemical substance sensing element 128 in accordance with the fourth embodiment. It is different from the fourth embodiment, however, in that two comb patterns including carbon nanostructures shown in FIGS. 8(A) to 8(C) are formed such that comb tines are arranged alternately.

FIG. 8(A) is a bird's eye view and FIG. 8(B) is a plan view of a chemical substance sensing element 142 used in the present embodiment. FIG. 8(C) is a cross sectional view in the direction of arrows along the line C-C of FIG. 8(B).

Referring to FIGS. 8(A) to 8(C), chemical substance sensing element 142 includes a plate-shaped substrate 150 having a thermally oxidized film formed on its surface, and comb patterns 152 and 153 including carbon nanostructure layer fabricated on the surface. Comb patterns 152 and 153 are formed such that tines extending from root portions are arranged alternately.

Referring to FIG. 7(C), substrate 150 includes a solid substrate 170 and a thermally oxidized film 172 formed on the surface of solid substrate 170.

Comb patterns 152 and 153 include a buffer layer 174 formed as a comb pattern on thermally oxidized film 172, a metal catalyst layer 176 formed on buffer layer 174, and a large number of carbon nanostructures 178 formed erected vertically on the surface of metal catalyst layer 176. Between tines of comb patterns 152 and 153, an opening 175 is formed. When carbon nanostructures are formed, carbon nanostructures 179 are also formed, which grow in the horizontal direction to bridge adjacent carbon nanostructures 178, included in each of the comb patterns 152 and 153, on opening 175. Buffer layer 174 is formed of an insulator.

Chemical substance sensing element 142 is arranged such that, of the patterns arranged adjacent to each other, one node 154 of comb pattern 152 is connected to a plus terminal of DC current such as DC power source 30 shown in FIG. 1 and one node 156 of comb pattern 153 is connected to load resistance 34, as shown in FIGS. 8(A) and 8(B). Nodes 154 and 156 are arranged to be connected to the layers of carbon nanostructures 178 and 179 shown in FIG. 8(C).

—Method of Manufacturing Chemical Substance Sensing Element 142—

Mainly referring to FIG. 8(C), chemical substance sensing element 142 is manufactured in the following manner. First, substrate 150 is prepared by forming thermally oxidized film 172 on solid substrate 170. Thermally oxidized film 172 is an insulator. In order to have carbon nanostructures grow on substrate 150, a mask having openings in accordance with a pattern is fabricated on the surface of thermally oxidized film 172, and buffer layer 174 is formed on thermally oxidized film 172. At this time, the mask pattern has such a shape as shown in FIG. 8(A), in which comb shapes are left with two combs alternately facing to each other, and opening 175 between combs is formed to have a large area.

After forming buffer layer 174, metal catalyst layer 176 is formed using the same mask pattern. After forming catalyst layer 176, carbon nanostructures 178 are formed on the surface of catalyst layer 176 using the same mask pattern. Finally, the mask pattern is removed.

Next, referring to FIG. 8(A), node 154 connected to comb pattern 152 is connected to a plus terminal of a DC power source, not shown, and node 156 connected to comb pattern 153 is connected to a minus terminal of the DC power source. Thereafter, a mixture of MePc solution and DAF-2 solution is dripped from directly above substrate 150 as shown in FIG. 8(C), using a pipette or the like to the surface of carbon nanostructures 178. Thereafter, a voltage from the DC power source is applied to chemical substance sensing element 142, and hence voltage is applied to carbon nanostructures. Then, the surfaces of carbon nanostructures are uniformly modified by MePc and DAF-2.

The reason is as follows. Roughly speaking, the carbon nanostructures include carbon nanostructures 178 grown vertically to the surface of metal catalyst layer 176 and carbon nanostructures 179 grown horizontally at the opening to bridge carbon nanostructures 178, as shown in FIG. 8(C). These carbon nanostructures are in contact with each other and, as mentioned above, carbon nanostructures are good conductor. Therefore, when a voltage is applied to chemical substance sensing element 142 under the presence of electrical connection as described above, current flows on the comb patterns and to the openings. On the other hand, MePc and DAF-2 as fluorescent molecules have polarities because of their molecular structures and, under electric field, they are drawn to the carbon nanostructures and modify the surfaces.

According to the fifth embodiment, it is possible to arrange a large number of carbon nanostructures on a small area. As a result, amount of specific chemical substance as the object of measurement increases and the change in electric resistance of comb patterns 152 and 153 increases. Therefore, the sensitivity of sensing the chemical substance can effectively be improved. Further, the carbon nanostructures grown in the horizontal direction are very thin and therefore, when chemical substance adheres thereto, electric resistance changes significantly. Therefore, use of these leads to higher sensitivity of sensing the specific chemical substance.

—Modification—

Figure 9:
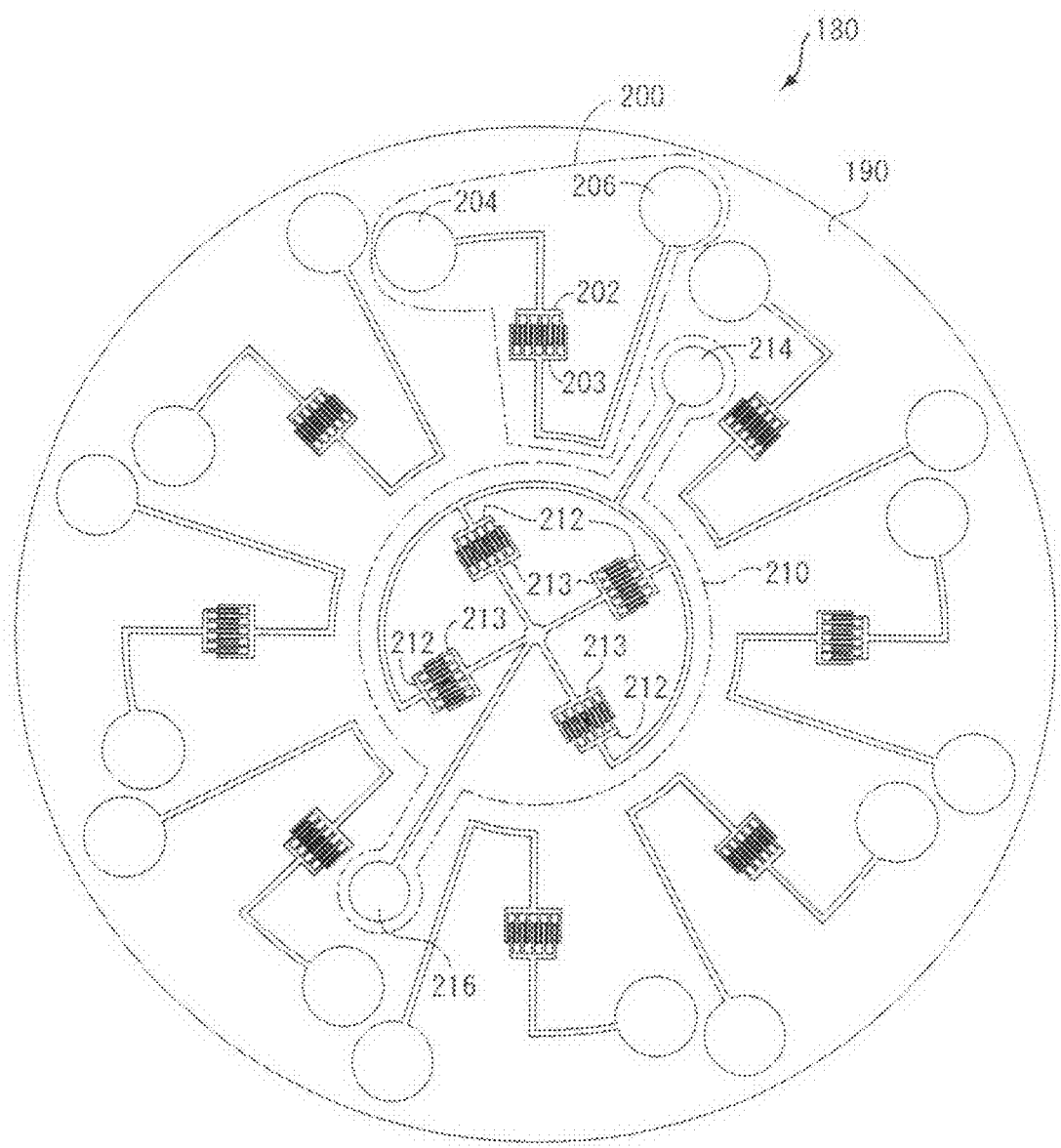
FIG. 9 shows a structure of a chemical substance sensing element 180 in accordance with a modification of the fifth embodiment.

Referring to FIG. 9, the chemical substance sensing element in accordance with the present embodiment may include: a plate shaped substrate 190 having a thermally oxidized film formed on its surface; and a plurality of chemical substance sensing elements 200 including comb patterns 202 and 203 with carbon nanostructures fabricated thereon, a node 204 connected to comb pattern 202 and a node 206 connected to comb pattern 203, fabricated on the substrate. The plurality of chemical substance sensing elements 200 may be arranged on substrate 190.

As another example, the chemical substance sensing element in accordance with the present embodiment may be arranged as follows. Substrate 190 is divided into inner and outer two areas, for example, as shown in FIG. 9, and a plurality of chemical substance sensing elements 200 are arranged on the outer area. On the inner area, a chemical substance sensing element 210 is arranged, which is similar to chemical substance sensing element 200 and has a plurality of combinations of comb patterns 212 and 213 with comb patterns 212 commonly connected to a node 214 and comb patterns 213 commonly connected to a node 216.

By such an arrangement, it is possible to detect a plurality of different chemical substances at the outer area and to detect with particularly high sensitivity a specific substance at the inner area.

Further, the present element may be a chemical substance sensing element 180 including a plurality of chemical substance sensing elements 200 and a chemical substance sensing element 210 as shown in FIG. 9.

Further, the present element may be manufactured in the similar manner as chemical substance sensing element 142, and it may be an element having an MePc modified unit and DAF-2 modified unit, by dripping MePc solution to a part and DAF-2 solution to the remaining part, of the comb patterns, when the surfaces of carbon nanostructures are modified. In that case, specific chemical substances may be detected in the following manner. The MePc modified unit is introduced to apparatus 20 shown in FIG. 1, in place of chemical substance sensing element 32. Apparatus 20 and MePc modified unit are introduced to container 64 shown in FIG. 4, and arranged in container 64 in place of chemical substance sensing unit 66. By applying a voltage to MePc modified unit from DC power source 30 and by directing excitation light 72 to DAF-2, the fluorescence excitation reaction and the change in electric resistance can simultaneously be measured. Thus, a specific chemical substance that reacts with fluorescent component and a specific chemical substance that reacts with MePc can simultaneously be measured.

EXAMPLES

Example 1

In the following, examples in accordance with the first embodiment will be described.

—Method of Manufacturing Chemical Substance Sensing Element 32—

Chemical substance sensing element 32 was manufactured by the method as described in the following. First, preparation was done for fabricating carbon nanostructures. On an Si substrate of 2 inches having a thermally oxidized film 172 of 300 nm in thickness formed on its surface, a metal mask of a desired pattern is placed, and by film formation for 2200 seconds with $SiO_2$ target using a high frequency sputtering machine (manufactured by ULVAC Technologies Inc., SBR2304/13.56 MHz, 200 W), a sputtered $SiO_2$ film of about 200 nm was further formed on the thermally oxidized film. Using an APG apparatus (manufactured by ULVAC Technologies Inc./discharge voltage 60V, anode-to-substrate distance 90 mm), Co was vapor-deposited to 5 nm and Ti was vapor-deposited to 1 nm in this order with the metal mask kept as it was, whereby catalyst layer 176 was formed.

Next, carbon nanostructures were formed. Using a microwave plasma-enhanced chemical vapor deposition (MW-CVD) apparatus, $H_2$ gas of about 50 sccm was introduced to a vacuum chamber through a mass flow controller, while maintaining substrate temperature at about 800° C. and pressure in vacuum chamber adjusted by a pressure control valve to be about 15 Torr. Next, by introducing microwave of 2.45 GHz (350 W), $H_2$ gas was turned to plasma, and the surface of a catalyst seed placed on the substrate was cleaned for about 5 minutes. Continuously thereafter, $CH_4$ gas diluted with $H_2$ ($H_2:CH_4$=50 sccm:50 sccm) as a raw material gas was turned to plasma for 5 minutes, so that carbon nanostructures in accordance with the pattern of catalyst layer were fabricated. Density of carbon nanostructures was $1\times10^{10}$ to $1\times10^{13}/cm^2$. Carbon nanostructures 178 formed in this manner were collected using tweezers.

Next, about 5 mg of thus collected carbon nanostructures were subjected to refluxing. Refluxing was done in the following manner. First, 5 mg of carbon nanostructures were subjected to ultrasonic cleaning in dilute nitric acid (35 vol %) of 20 mL, and subjected to refluxing at 100° C. for 5 hours. Thereafter, by drawing a polytetrafluoroethylene (hereinafter denoted as "PTFE") film having pore diameter of 0.2 μm with a vacuum pump, filtering was done. Then, carbon nanostructures left on the PTFE film were cleaned together with the PTFE film using deionized water, to pH7. The PTFE film was rinsed with 15 mL of acetone, and dried overnight at 60° C., and carbon nanostructures were scraped off therefrom and subjected to reflux with 20 mL of 30% hydrogen peroxide solution at 100° C. for 180 minutes. Filtering with PTFE film was again performed, followed by rinsing with 30 mL of deionized water and cleaning with 15 mL of acetone, and the result was dried at 60° C., whereby final carbon nanostructures were obtained.

Carbon nanostructures were surface-modified in the following manner. Cobalt phthalocyanine (hereinafter denoted as "CoPc") was developed to the concentration of 0.1 mM in tetrahydrofuran (hereinafter denoted as "THF") solution, whereby a solution was prepared. To the solution, carbon nanostructures of 5 mg were put in, and the carbon nanostructures were uniformly dispersed in the solution using ultrasonic cleaner.

Figure 10:
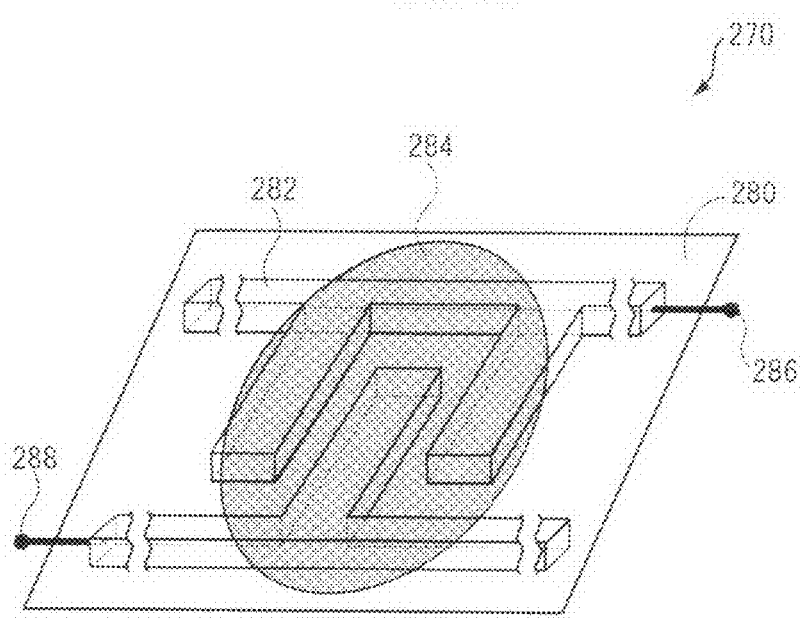
FIG. 10 is a schematic illustration related to a part of the method of manufacturing a chemical substance sensing element 270 of Example 1 in accordance with the first embodiment.

Next, the chemical substance sensing element 270 in accordance with the present example was fabricated in the following manner. Referring to FIG. 10, on a substrate 280, Au electrodes 282 were formed beforehand in a pattern of two combs facing to each other with a pitch of 100 μm, by vapor deposition using a shadow mask. Then, a solution 284 of 100 μL containing the carbon nanostructures surface-modified with CoPc molecules was dripped from above and the solvent in the solution was dried, whereby chemical substance sensing element 270 was obtained.

A portion of Au electrode 282 shown in FIG. 10 on which solution 284 was dripped so that solution 284 adheres to electrode 282 was used as a portion corresponding to chemical substance sensing unit 42 shown in FIG. 2, and a portion close to one end 286 and a portion close to the other end 288 of two combs at areas of Au electrode 282 where solution 284 does not adhere to are used as electrodes 40*a* and 40*b* shown in FIG. 2, respectively. In this manner, manufacturing of chemical substance sensing element was finished. In the following, the chemical substance sensing element manufactured in the above-described manner will be referred to as chemical substance sensing element 32.

In the following examples, the method of manufacturing the portion related to sensing of a chemical substance is the same as in Example 1. Therefore, in the following description of examples, details thereof will not be repeated.

—Method of Evaluation—

The method of evaluating characteristics of chemical substance sensing element 32 will be described. Apparatus 20 shown in FIG. 1 was inserted to a chamber of stainless (Stainless Used Steel: SUS) of about 20 liters, which allows atmosphere control, and the atmosphere around the chemical substance sensing element was once set to a vacuum state of about $10^{-3}$ Torr using a diaphragm pump. A current of 200 μA was caused to flow from DC power source 30, a change in electric resistance at a node between chemical substance sensing element 32 and load resistance 34 was amplified by amplifier 36, and the amplified change in electric resistance was measured as a change in output voltage of amplifier 36, by a DC voltmeter, not shown. Initial resistance of chemical substance sensing element was Ro=20 kΩ, and the measurement was done at a frequency of once in every second, for 60 seconds. The measured value was used as the initial value. Next, a gas as the object of measurement having pentane concentration of 100 ppb sealed in a Tedlar bag of 1 liter was introduced little by little to the chamber while monitoring a pressure gauge, and introduction was terminated when atmospheric pressure was attained.

The gas as the object of sensing was prepared in the following manner. Pentane standard gas diluted with nitrogen to the concentration of 1 ppm and nitrogen gas were mixed at a ratio of 1/10, whereby the pentane standard gas was diluted to the gas having pentane concentration of 100 ppb, as the object of sensing.

In this state, the change in output voltage of amplifier 36 was measured under the same conditions, in the similar manner as when the standard value was measured.

FIG. 11 plots the difference from the initial value.

—Result of Evaluation—

Referring to FIG. 11, measurement value 300 indicates the change in electric resistance. It can be seen from FIG. 11 that chemical substance sensing element 32 of the present example is capable of confirming presence of pentane, and lower detection limit thereof was, in the present experimental system, equal to or lower than 100 ppb.

As described above, the chemical substance sensing element in accordance with the first embodiment can confirm presence of pentane in the atmosphere, and has higher sensitivity than the prior art.

In the following examples, the method of manufacturing the portion related to sensing of chemical substance and the method of introducing a gas as an object of measurement to the vicinity of the portion related to sensing of chemical substance are the same as in Example 1 and, therefore, in the following description of examples, details thereof will not be repeated.

Example 2

In the following, an example in accordance with the second embodiment will be described.

—Method of Manufacturing Chemical Substance Sensing Unit 66—

The method of manufacturing chemical substance sensing unit 66 in accordance with the present example will be described in the following. Similar to the method of manufacturing chemical substance sensing element 32 of Example 1, preparation for fabricating carbon nanostructures, fabrication of carbon nanostructures and refluxing of carbon nanostructures were performed. Next, a DAF-2 solution of 5 mmoL prepared by developing 1 mg of DAF-2 in 550 μL of dimethyl sulfoxide (hereinafter denoted as "DMSO") was diluted 500 times (about 10 μmol/L) with phosphate buffer solution (0.1 mol/L). Carbon nanostructures of 5 mg was put into the solution, and dispersed using an ultrasonic cleaner. The dispersed liquid was filtered by a PTFE film and dried, and thus, chemical substance sensing unit 66 was obtained.

—Method of Evaluation—

The method of evaluating characteristics of chemical substance sensing apparatus 62 will be described. Referring to FIG. 4, to a container 64 having chemical substance sensing unit 66 arranged therein, a gas as an object of measurement having NO concentration of 100 ppb, diluted with nitrogen was introduced. Immediately thereafter, excitation light 72 having the wavelength of 495 nm was directed to chemical substance sensing unit 66. Presence/absence of fluorescence 73 and its wavelength at this time were inspected using display system 71.

—Result of Evaluation—

As a result of the process above, fluorescence having the wavelength of 515 nm was observed. Therefore, it was found that the chemical substance sensing element of the present example was capable of confirming presence of NO and lower detection limit thereof was, in the present experimental system, equal to or lower than 100 ppb.

As described above, the chemical substance sensing element in accordance with the second embodiment can confirm presence of NO in the atmosphere, and has higher sensitivity than the prior art.

Example 3

An example in accordance with the third embodiment will be described in the following.

—Method of Manufacturing Chemical Substance Sensing Element 108—

Figure 6:
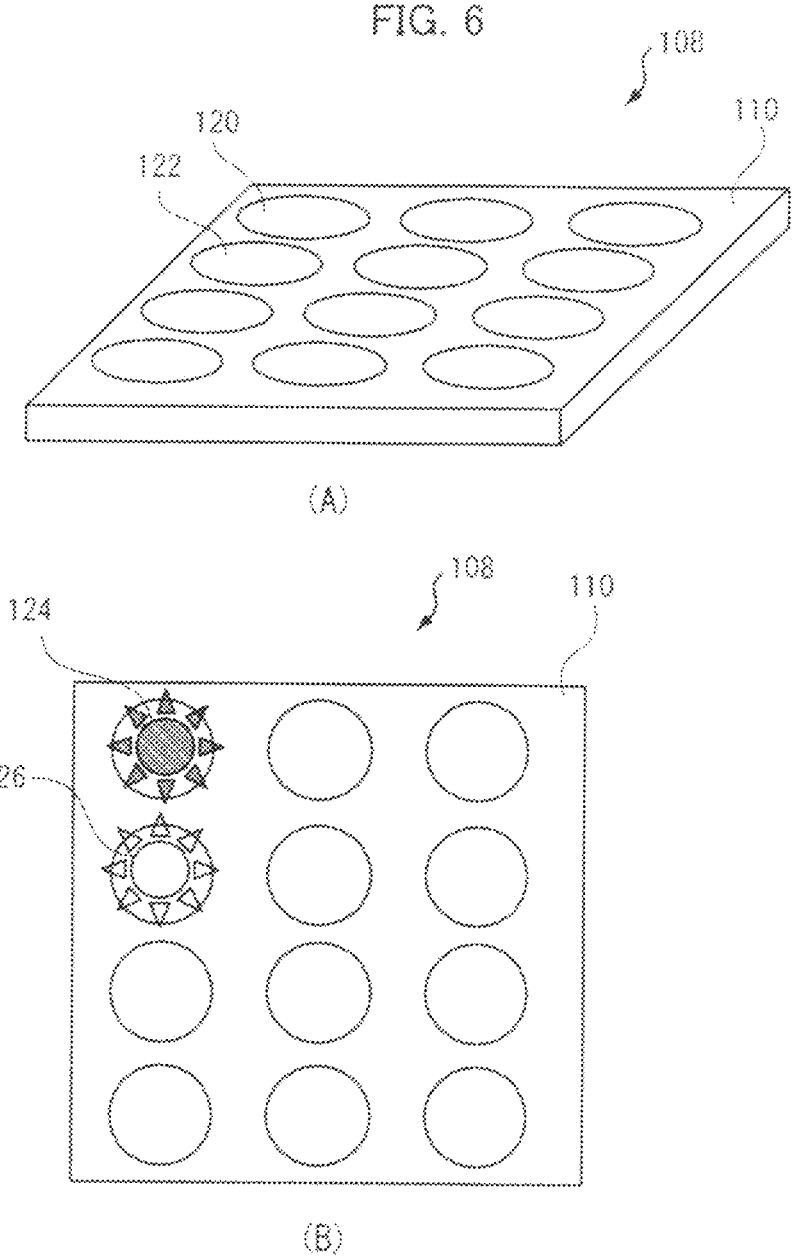
FIG. 6 is an illustration related to the structure and operation of a chemical substance sensing element 108 in accordance with a third embodiment.

A method of manufacturing chemical substance sensing element 108 will be described. First, a chemical substance sensing unit for sensing NO was fabricated in the similar manner as in Example 2 and placed in well 120, as shown in FIG. 6.

Next, a chemical substance sensing unit for sensing acetone was fabricated in the following manner. First, similar to the method of manufacturing chemical substance sensing element 32 of Example 1, preparation for fabricating carbon nanostructures, fabrication of carbon nanostructures and refluxing of carbon nanostructures were performed. Next, DNPH-sulfuric acid reagent was applied to the surface of carbon nanostructures, to provide the chemical substance sensing unit for sensing acetone. This was placed in well 122, and manufacturing of chemical substance sensing element 108 was finished.

—Method of Evaluation—

The method of evaluating characteristics of chemical substance sensing element 108 of the present example will be described in the following. In the present embodiment also, an apparatus having a similar structure as chemical substance sensing apparatus 62 shown in FIG. 4 is used. Referring to FIG. 4, chemical substance sensing element 108 is placed in container 64. To container 64, a gas as the object of measurement having NO and acetone concentration of 100 ppb diluted with nitrogen was introduced and immediately thereafter, UV light (wavelength 200 nm to 800 nm) was directed as excitation light to chemical substance sensing element 108. Presence/absence of fluorescence 73 and its wavelength at this time were inspected using display system 71.

—Result of Evaluation—

Referring to FIG. 4, when the wavelength of excitation light 72 was 440 nm, yellowish orange fluorescence 126 was observed at well 122 and when it was 495 nm, green fluorescence 124 was observed at well 120. Therefore, it was found that the chemical substance sensing element of the present example is capable of confirming presence of NO and acetone, and lower detection limit thereof was, in the present experimental system, equal to or lower than 100 ppb.

As described above, the chemical substance sensing element in accordance with the third embodiment can confirm presence of NO and acetone in the atmosphere, and has higher sensitivity than the prior art.

Further, the chemical substance sensing element in accordance with Example 3 allows easy sensing at one time even when the gas as the object of sensing is a mixture of a plurality of substances.

Example 4

In the following, an example in accordance with the fifth embodiment will be described.

—Method of Manufacturing Chemical Substance Sensing Element 142—

The method of manufacturing chemical substance sensing element 142 will be described in the following. Similar to the method of manufacturing chemical substance sensing element 32 of Example 1, preparation for fabricating carbon nanostructures, fabrication of carbon nanostructures and refluxing of carbon nanostructures were performed. Here, substrate temperature at the time of film-forming for carbon nanostructures was set to 500° C. to 1000° C., rather than 800° C. The carbon nanostructures manufactured at this time included carbon nanostructures 178 grown vertically to the surface in comb patterns with their length made uniform to about 100 μm and carbon nanostructures 179 grown horizontally at openings.

Next, from above the patterns of carbon nanostructures, 100 μL of the following mixture liquid was dripped. Specifically, it is a mixture of a CoPc solution developed to the concentration of 0.1 mM in THF solution, and a solution (about 5 mmol/L) of 1 mg of DAF-2 developed in 0.45 mL of DMSO diluted 500 times with phosphate buffer solution (0.1 mol/L). Thereafter, as shown in FIG. 8(A), node 154 connected to comb pattern 152 was connected to a plus terminal of the DC power source and node 156 connected to comb pattern 153 was connected to a minus terminal of the DC power source, a voltage of 5V was applied from the DC power source to cause a current flow through the carbon nanostructures, so that the surfaces of carbon nanostructures were uniformly modified with CoPc and DAF-2. The result was used as chemical substance sensing element 142.

—Method of Evaluation—

Evaluation was done in the similar manner as in Example 1, using a gas as an object of sensing diluted with nitrogen, having NO concentration of 100 ppb. Change in electric resistance similar to that shown in FIG. 11 was observed. Thus, it was found that the chemical substance sensing element of the present example is capable of confirming presence of NO, and lower detection limit thereof was, in the present experimental system, equal to or lower than 100 ppb.

As described above, the chemical substance sensing element in accordance with the fifth embodiment can confirm presence of NO in the atmosphere, and has higher sensitivity than the prior art.

Comparison Between Manufacturing Methods of Examples 2 and 4

The manners of surface modification with DAF-2 in chemical substance sensing elements 32 and 142 fabricated as Examples 2 and 4 were evaluated and compared, using an energy filtering type transmission electron microscope (EF-TEM), an electron scanning microscope (SEM), a Raman spectrometer, an FT-IR apparatus, a fluorescent X-ray analyzer (FX) and an X-ray diffractometer (XD). As a result, it was confirmed that in chemical substance sensing element 32 in accordance with Example 2, the DAF-2 layer has film thickness distribution in the range of about 10 to about 50 nm. On the other hand, in chemical substance sensing element 142, it was confirmed that the DAF-2 layer was formed to have an average film thickness of about 5 nm, and that the film thickness was thinner and more uniform than in chemical substance sensing element 32.

From the foregoing, it was understood that in chemical substance sensing of Example 4, specific surface area of CNT that can react with NO is larger than the method of Example 2 and, therefore, the state of components in the atmosphere can better be reflected.

As described above, according to the present invention, for sensing a specific substance included in biological information, a chemical substance sensing element formed of carbon nanostructures having marker selectivity and high sensitivity, that were difficult to attain by the prior art, can be provided. This element enables chemical substance sensing with marker selectivity on markers such as NO, pentane and acetone. In addition, as the sensitivity can be improved by surface processing, it becomes possible to sense a very small amount of marker, of which detection has been difficult to date.

In the embodiments above, the chemical substance sensing element was formed by using carbon nanostructures as a base body and modifying the surface with metal complex or its derivative, or fluorescent molecule that has the characteristic of generating fluorescence when bonded to a specific substance. Though it is desirable to use carbon nanostructures as the base body since use of carbon nanostructures improves sensitivity, in principle, any substance may be used as the base body provided that the substance has high affinity to the molecules used for surface modification.

According to the embodiments of the present invention, it is possible to detect with high sensitivity a specific substance derived from a disease. This enables an individual to easily check his/her health condition, and hence, it contributes to early detection and rapid cure of diseases.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

Industrial Applicability

The present invention is applicable to sensing of a chemical substance in gas and liquid biological samples, to check human health condition.

The invention claimed is:

1. A chemical substance sensing apparatus, comprising:
a chemical substance sensing element for detecting a specific chemical substance, including an electrically conductive sensing body surface-modified with metal complex or its derivative and a fluorescent molecule;
detecting means, electrically connected to said chemical substance sensing element, for detecting a change in electric resistance of said chemical substance sensing element;
fluorescence detecting means arranged to allow detection of fluorescence generated by excitation light from said fluorescent molecule bonded to said chemical substance sensing element; and
determining means, connected to said fluorescence detecting means, for determining presence/absence of the fluorescence of a specific wavelength; wherein
said fluorescent molecule is capable of selective bonding to the specific chemical substance and product of bonding generates fluorescence of the specific wavelength upon irradiation with said excitation light.

2. The chemical substance sensing apparatus according to claim 1, further comprising
light emitting means, arranged at a position allowing, with light emitted therefrom, irradiation of said chemical substance sensing element, for emitting said excitation light to said fluorescent molecule.

3. The chemical substance sensing apparatus according to claim 1, wherein
said sensing body includes a carbon nanostructure.

4. The chemical substance sensing apparatus according to claim 1, wherein said metal complex consists of metal phthalocyanines.

5. The chemical substance sensing apparatus according to claim 1, wherein said fluorescent molecule is diaminofluorescein-2.

6. The chemical substance sensing apparatus according to claim 1, further comprising means for heating, for irradiating with light or for evacuating said chemical substance sensing element, whereby substance adsorbed on a surface of said chemical substance sensing element is substantially removed.

* * * * *